(12) United States Patent
Kipp et al.

(10) Patent No.: US 7,511,079 B2
(45) Date of Patent: Mar. 31, 2009

(54) METHODS AND APPARATUSES FOR THE COMMINUTION AND STABILIZATION OF SMALL PARTICLES

(75) Inventors: James E. Kipp, Wauconda, IL (US); Joseph Chung Tak Wong, Gurnee, IL (US); Monte Wisler, Lake Villa, IL (US); Rhonda Garcia, Mundelein, IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 10/806,050

(22) Filed: Mar. 22, 2004

(65) Prior Publication Data

US 2004/0266890 A1 Dec. 30, 2004

Related U.S. Application Data

(60) Provisional application No. 60/457,424, filed on Mar. 24, 2003.

(51) Int. Cl.
*B01F 3/12* (2006.01)
*B01F 3/08* (2006.01)

(52) U.S. Cl. .................. 516/53; 516/924; 516/925; 977/840

(58) Field of Classification Search ............ 516/53, 516/924, 925
See application file for complete search history.

(56) References Cited

U.S. PATENT DOCUMENTS

| 3,685,261 A * | 8/1972 | McIlvaine et al. ............. 96/262 |
| 4,908,154 A | 3/1990 | Cook et al. |
| 5,314,506 A | 5/1994 | Midler, Jr. et al. |
| 5,720,551 A | 2/1998 | Shechter |
| 5,780,062 A | 7/1998 | Frank et al. |
| 5,833,891 A | 11/1998 | Subramaniam et al. |
| 5,858,410 A | 1/1999 | Muller et al. |
| 6,086,376 A | 7/2000 | Moussa et al. |
| 6,221,332 B1 | 4/2001 | Thumm et al. |
| 6,221,398 B1 | 4/2001 | Jakupovic et al. |
| 2002/0012675 A1 | 1/2002 | Jain et al. |
| 2002/0012704 A1 | 1/2002 | Pace et al. |
| 2002/0041896 A1 | 4/2002 | Straub et al. |
| 2002/0054912 A1 | 5/2002 | Kim et al. |
| 2002/0176935 A1 | 11/2002 | Kipp et al. |
| 2003/0031719 A1 | 2/2003 | Kipp et al. |
| 2003/0044433 A1 | 3/2003 | Werling et al. |

FOREIGN PATENT DOCUMENTS

| EP | 0169 618 | 11/1993 |
| WO | WO 99/30833 | 6/1999 |
| WO | WO 01/62374 | 8/2001 |
| WO | PCT/US2004/009242 | 1/2005 |

OTHER PUBLICATIONS

Emulsifying Cell Operating Manual, Best Emulsifuing Equipment International, Midgdal Haemek, Israel, pp. 3-21.
Irwin J. Gruverman, "Breakthrough Ultraturbulent Reaction Technology Opens Frontier for Developing Life-Saving Nanometer-Scale Suspensions & Dispersons", Drug Delivery Technology, pp. 1-10 Copyright 2001-2005, Retrieved Jan. 4, 2006.

* cited by examiner

*Primary Examiner*—Timothy J. Kugel
(74) *Attorney, Agent, or Firm*—Marshall, Gerstein & Borun LLP

(57) ABSTRACT

Methods and apparatuses for comminuting and stabilizing small particles are provided. In one embodiment, an apparatus moves an organic compound dissolved in a solvent to form a suspension of particles in a first fluid stream and moves the suspension in a second fluid stream, wherein the second fluid stream is oriented and positioned with respect to the first stream to cause shearing between the streams and mixing of at least some of the particles in the first and second streams.

14 Claims, 18 Drawing Sheets

Figure 18:
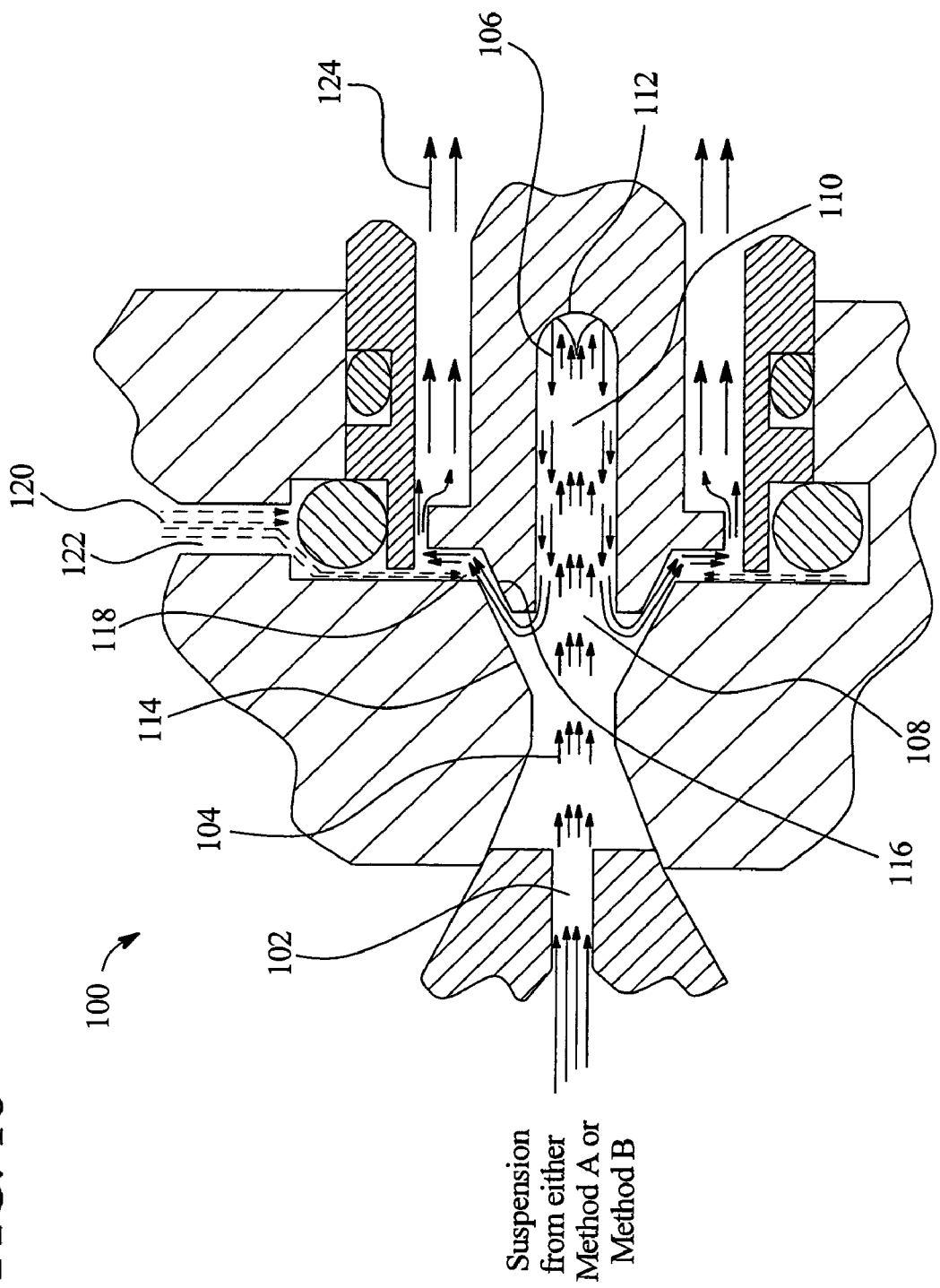
Figure 19:
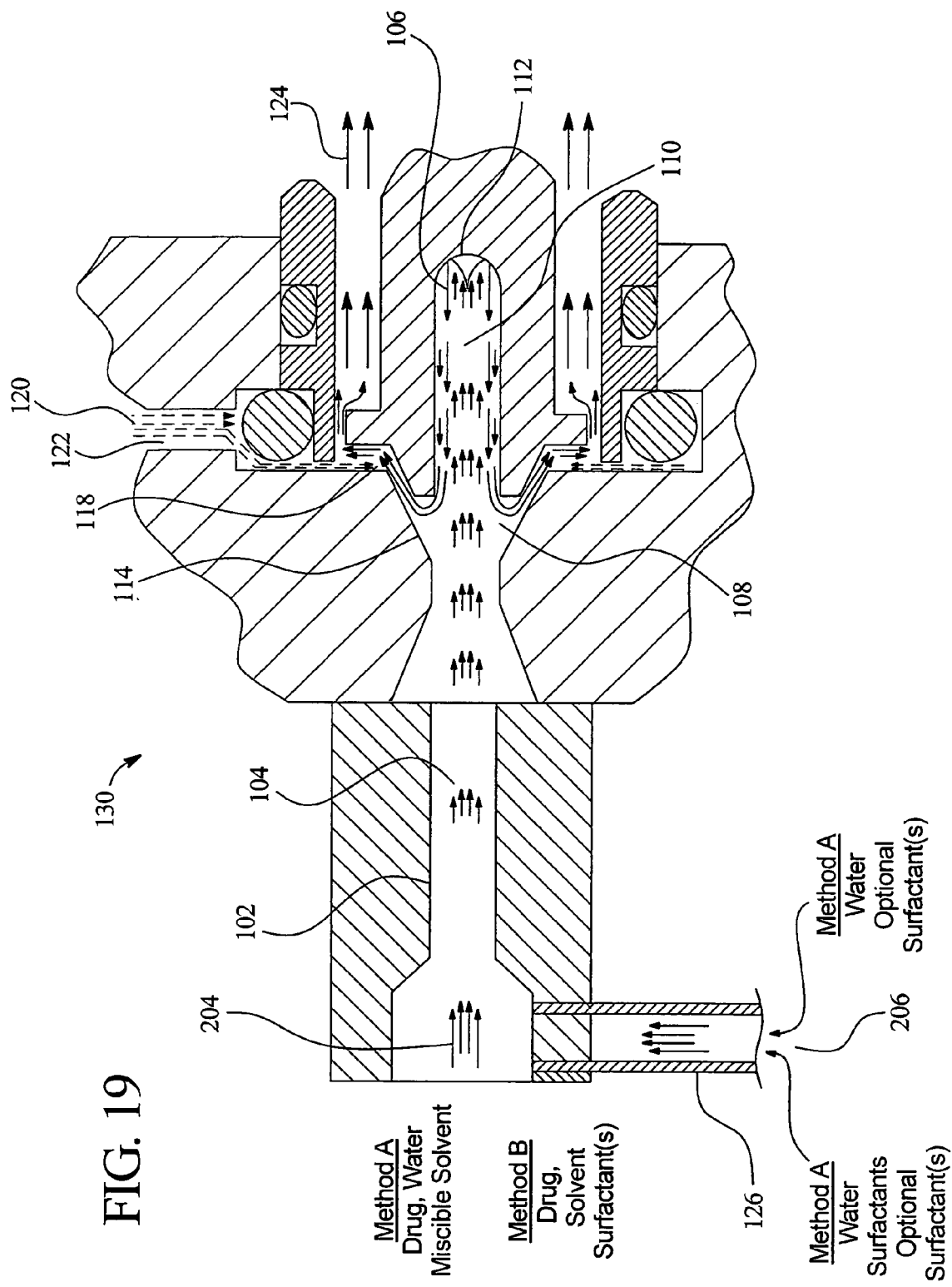

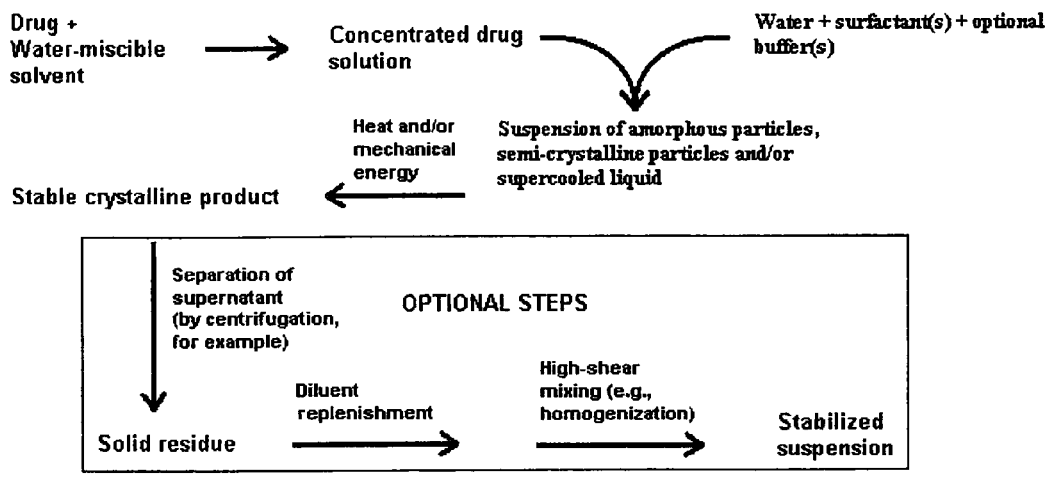
Figure 1: Method A:
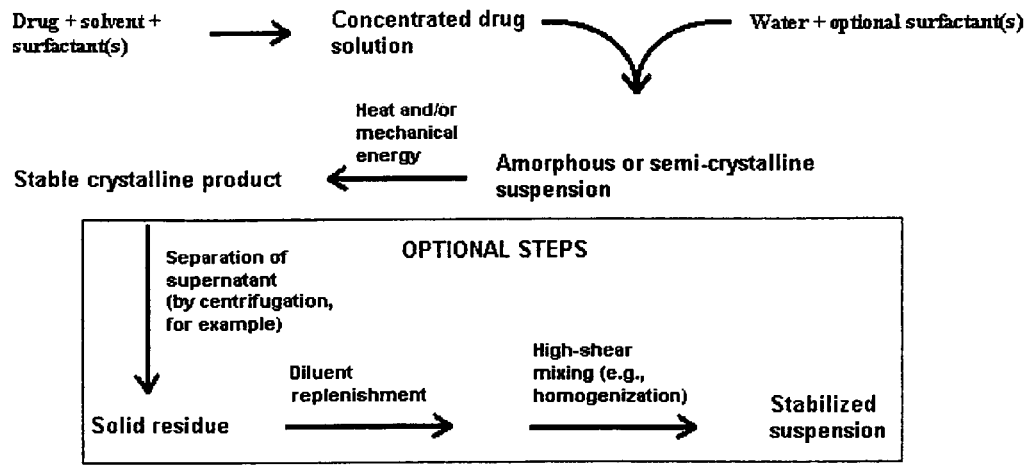
Figure 2: Method B:

Figure 3: Amorphous particles prior to homogenization (Example 1).
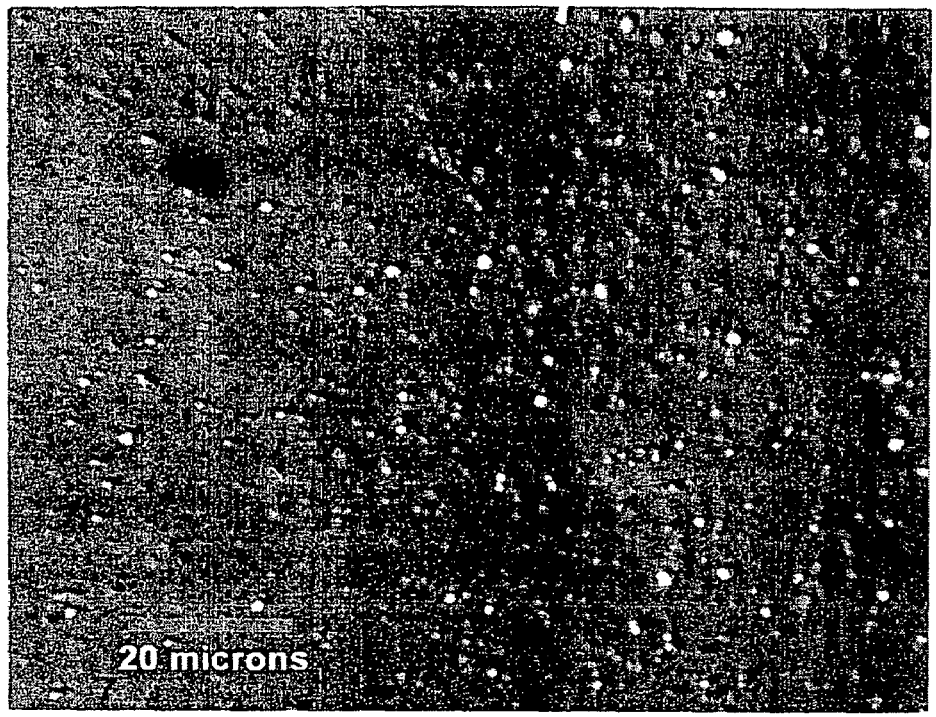
Figure 4: Particles after annealing by homogenization.
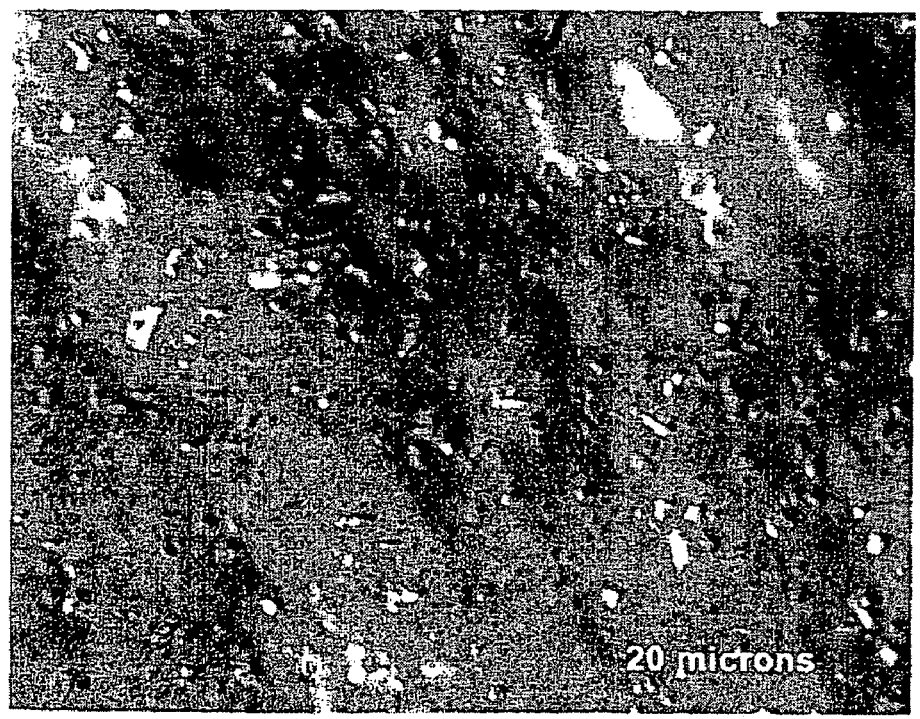

Figure 5: X-Ray diffractogram of microprecipitated itraconazole with polyethylene glycol-660 12-hydroxystearate before and after homogenization (Example 5).
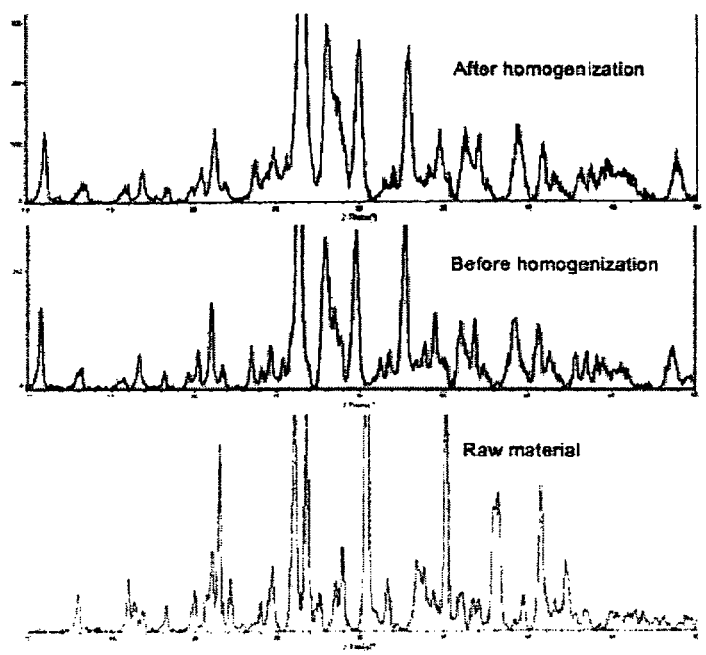

Figure 6: Carbamazepine crystals before homogenization (Example 6).
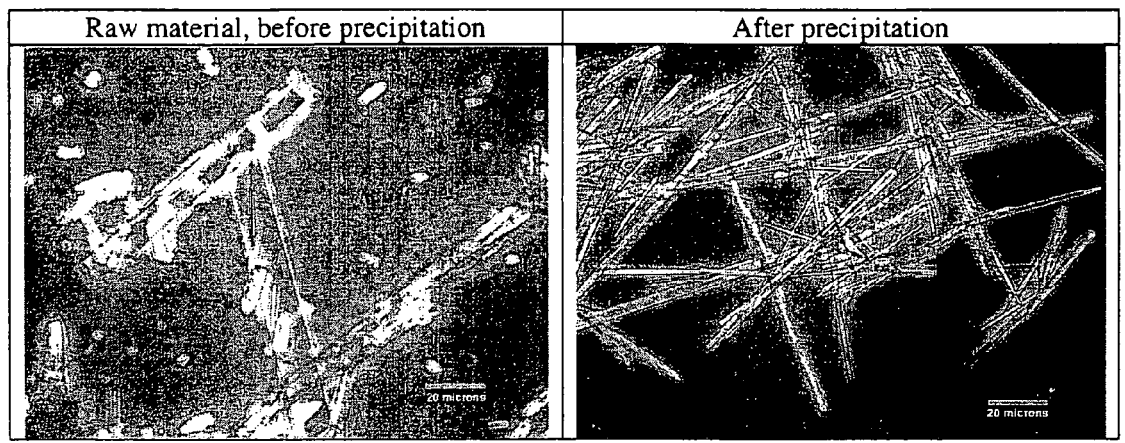
Figure 7: Carbamazepine microparticulate after homogenization (Avestin C-50)
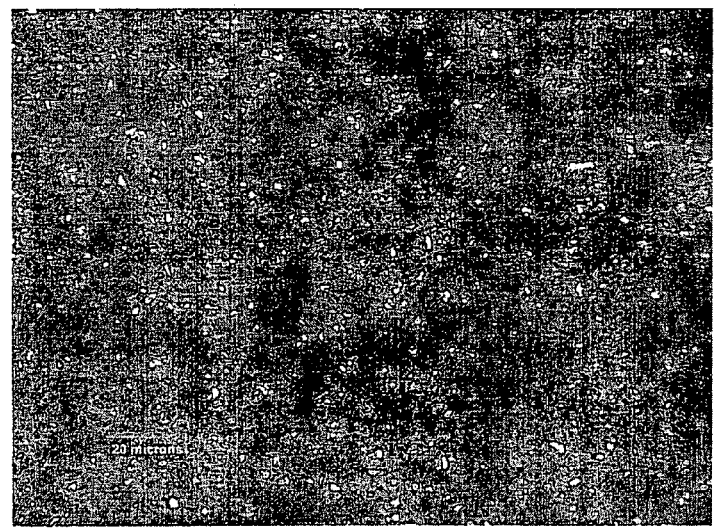
(Example 6).

Figure 8: Diagram of Microprecipitation Process for Prednisolone (Examples 9-12)
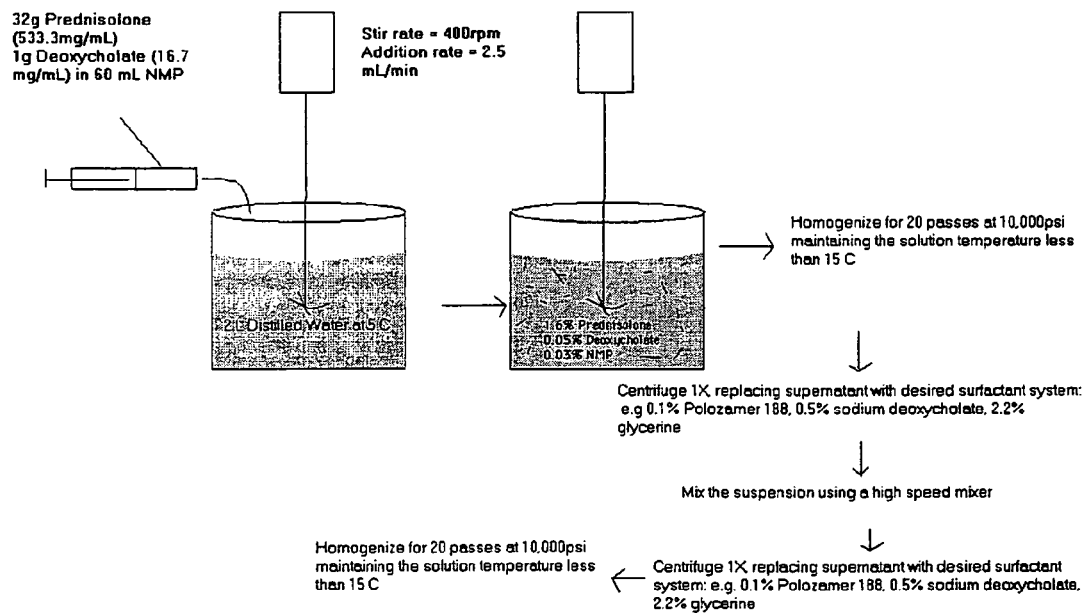

Figure 9: Photomicrograph of prednisolone suspension before homogenization (Hoffman Modulation Contrast, 1250X magnification)
Figure 10: Photomicrograph of prednisolone suspension after homogenization (Hoffman Modulation Contrast, 1250X magnification).
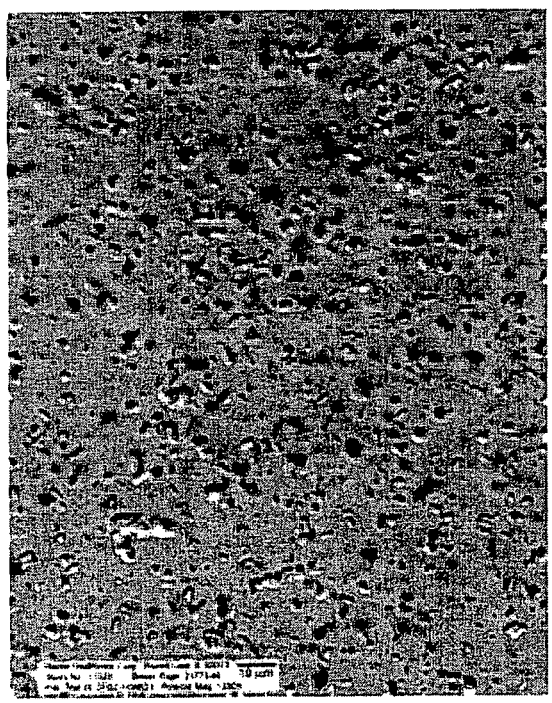

Figure 11: Comparison of size distributions of nanosuspensions (this invention) and commercial fat emulsion. (Example 13)
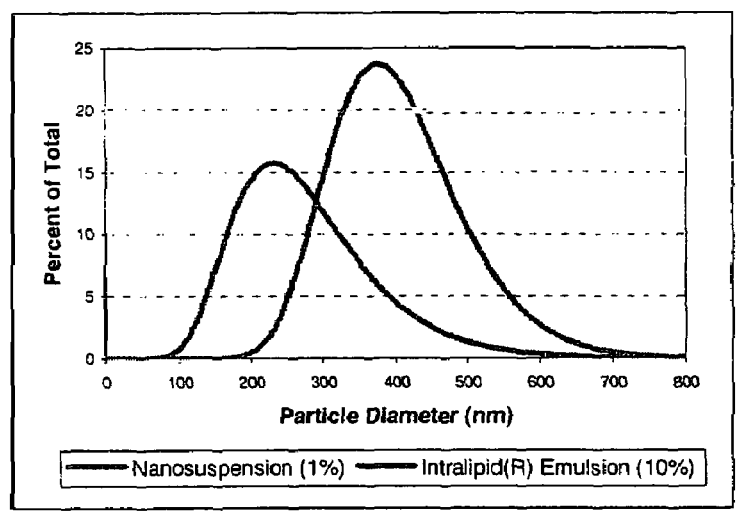

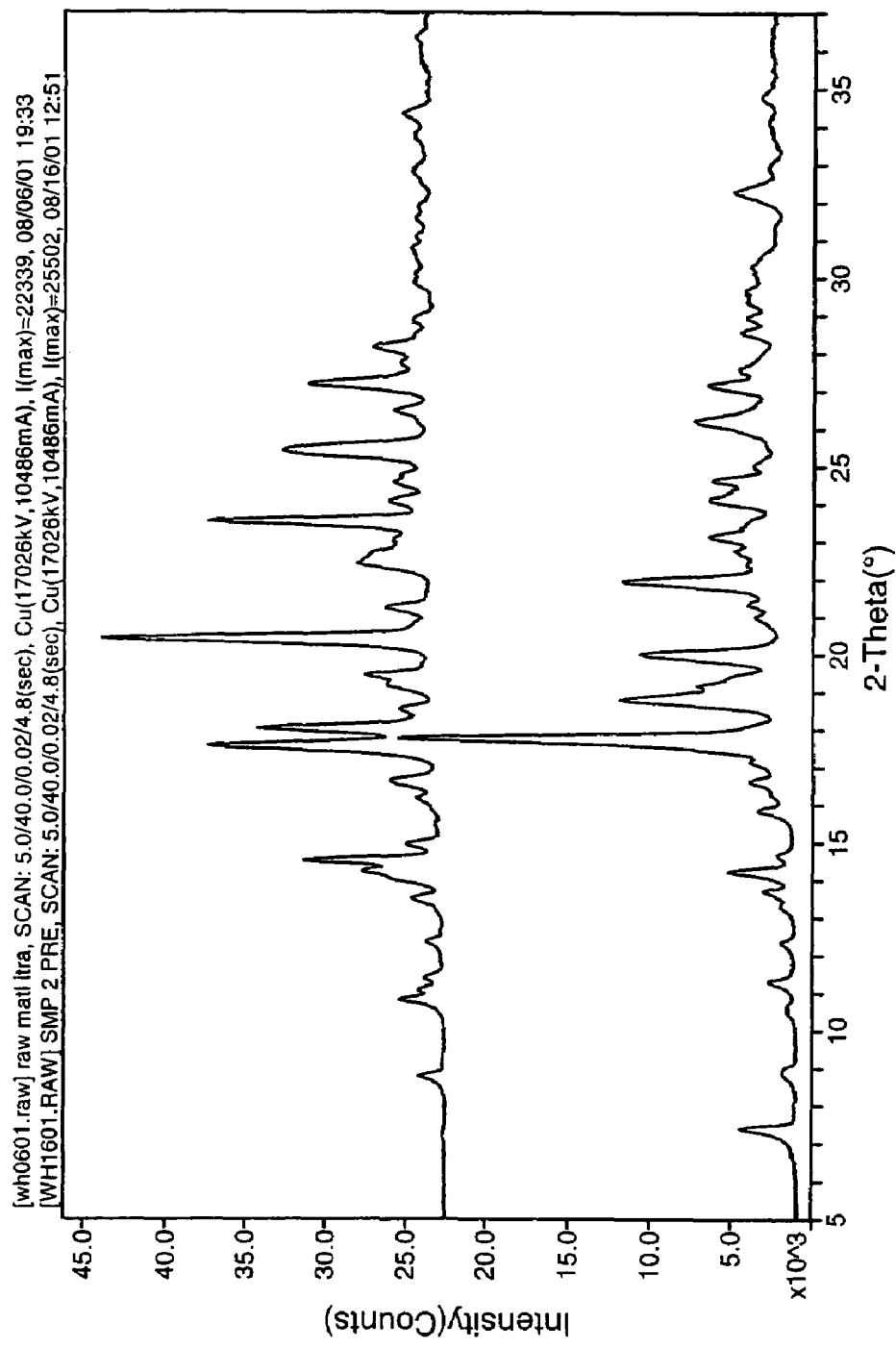
Figure 12: X-ray powder diffraction patterns for raw material itraconazole (top) and SMP-2-PRE (bottom). The raw material pattern has been shifted upward for clarity. (Example 16)

Figure 13a: DSC trace for raw material itraconazole (Example 16)
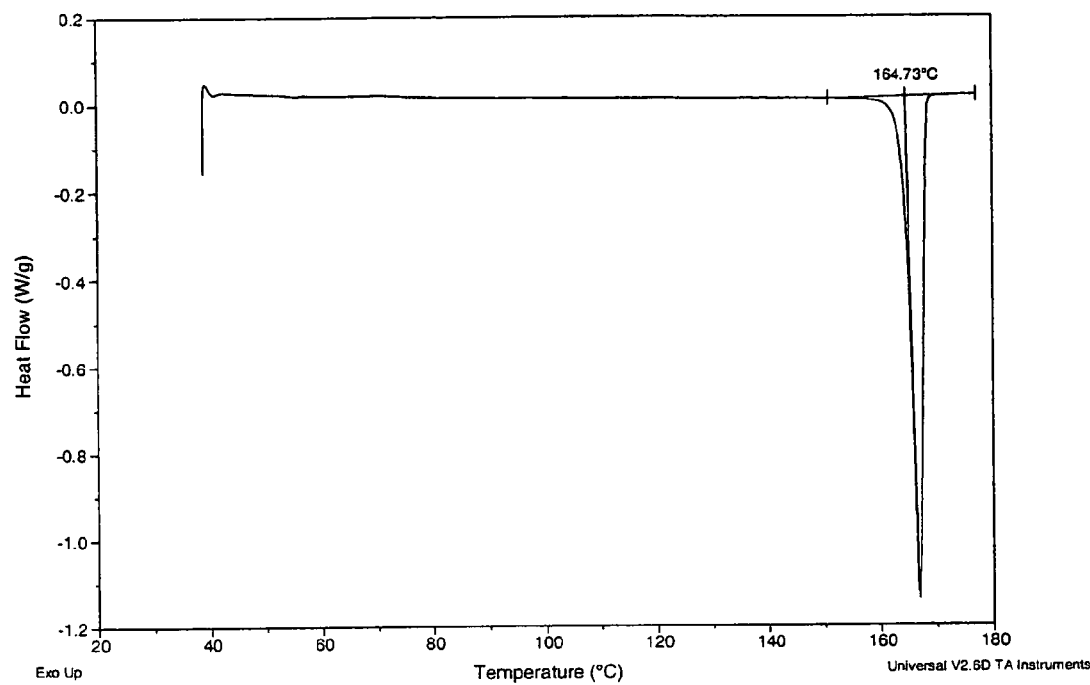
Figure 13b: DSC trace for SMP-2-PRE. (Example 16)
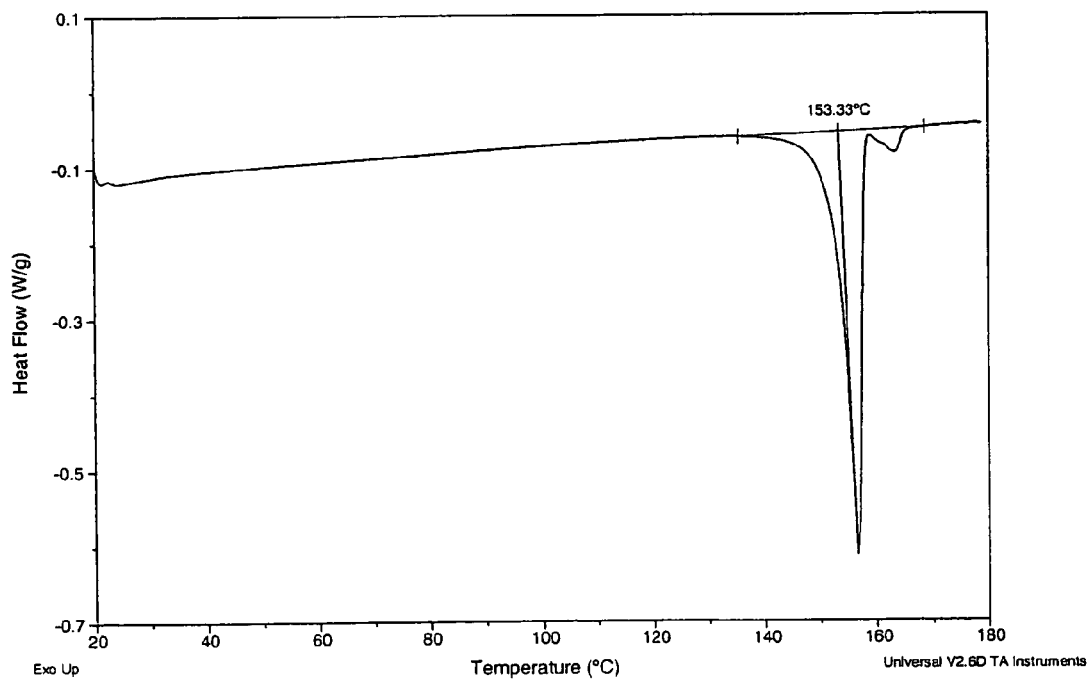

Figure 14: DSC trace for SMP-2-PRE showing the melt of the less stable polymorph upon heating to 160 °C, a recrystallization event upon cooling, and the subsequent melting of the more stable polymorph upon reheating to 180 °C. (Example 16)
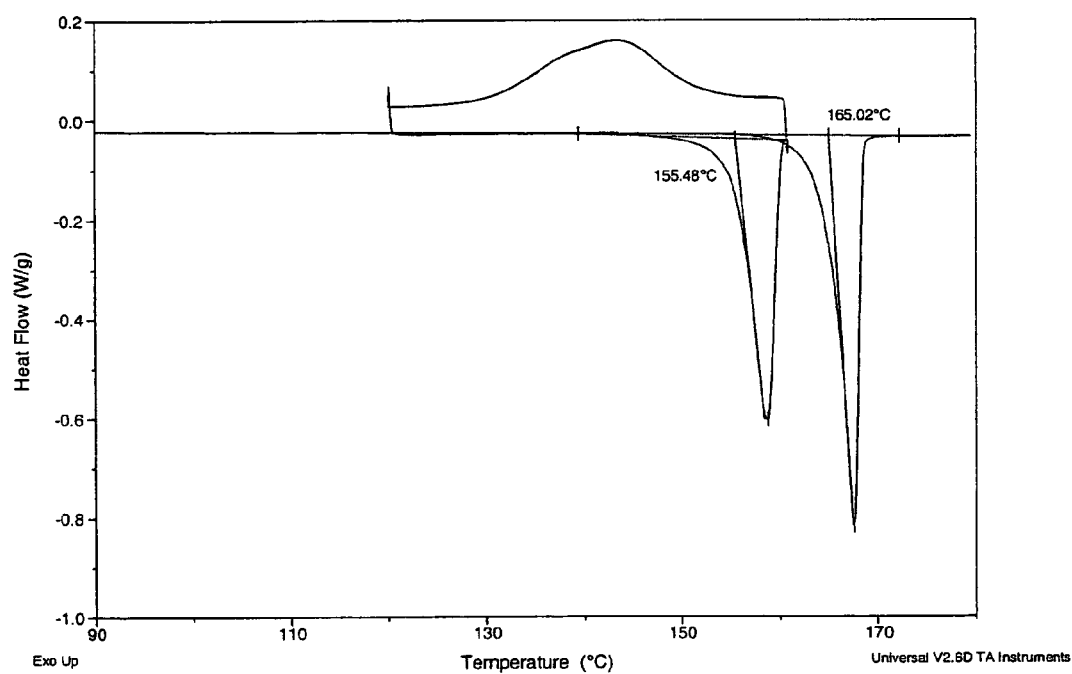

Figure 15: Comparison of SMP-2-PRE samples after homogenization. Solid line = sample seeded with raw material itraconazole. Dashed line = unseeded sample. The solid line has been shifted by 1 W/g for clarity (Example 16)
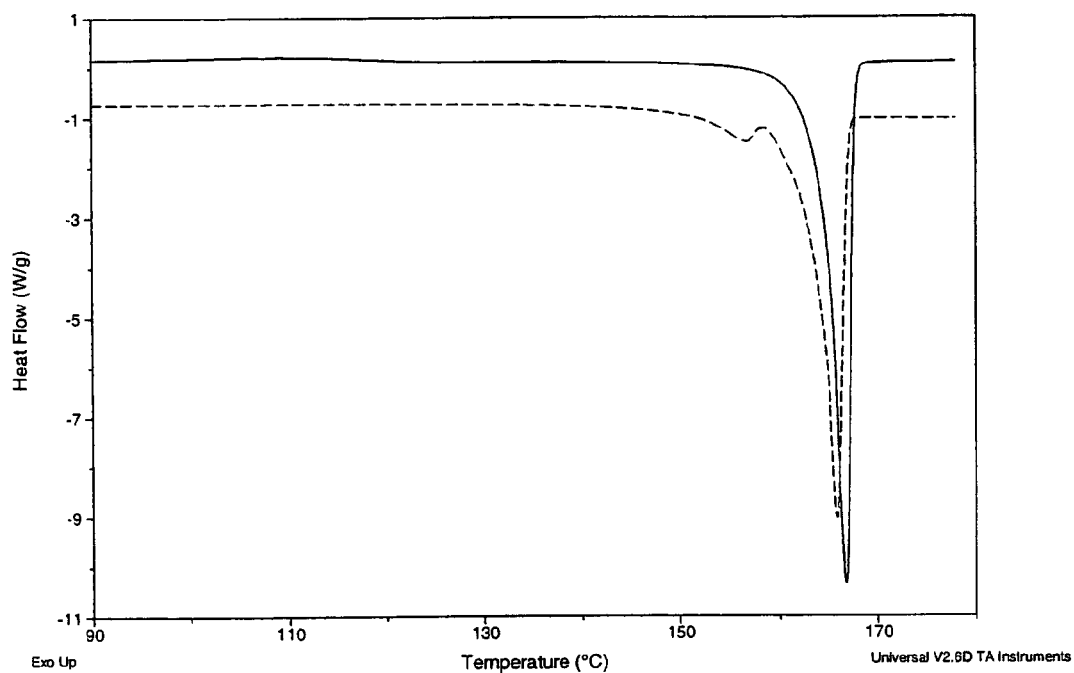

Figure 16: Effect of seeding during precipitation. Dashed line = unseeded sample, solid line = sample seeded with raw material itraconazole. The unseeded trace (dashed line) has been shifted upward by 1.5 W/g for clarity. (Example 17)
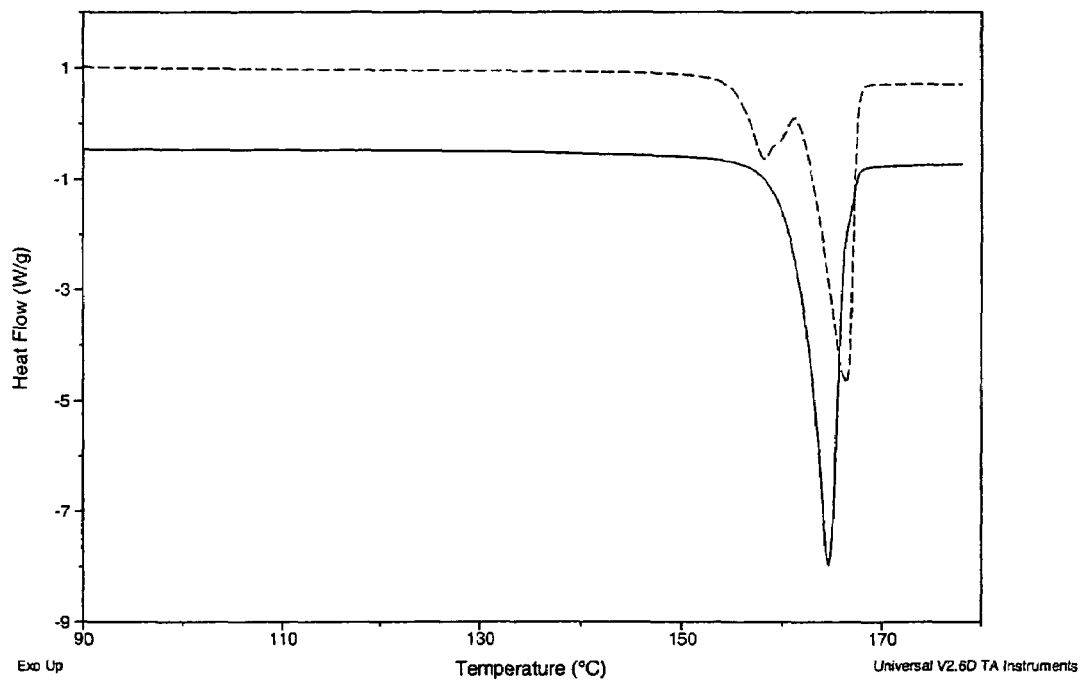

Figure 17: Effect of seeding the drug concentrate through aging. Top x-ray diffraction pattern is for crystals prepared from fresh drug concentrate, and is consistent with the stable polymorph (see Figure 12, top). Bottom pattern is for crystals prepared from aged (seeded) drug concentrate, and is consistent with the metastable polymorph (see Figure 12, bottom). The top pattern has been shifted upward for clarity. (Example 18)

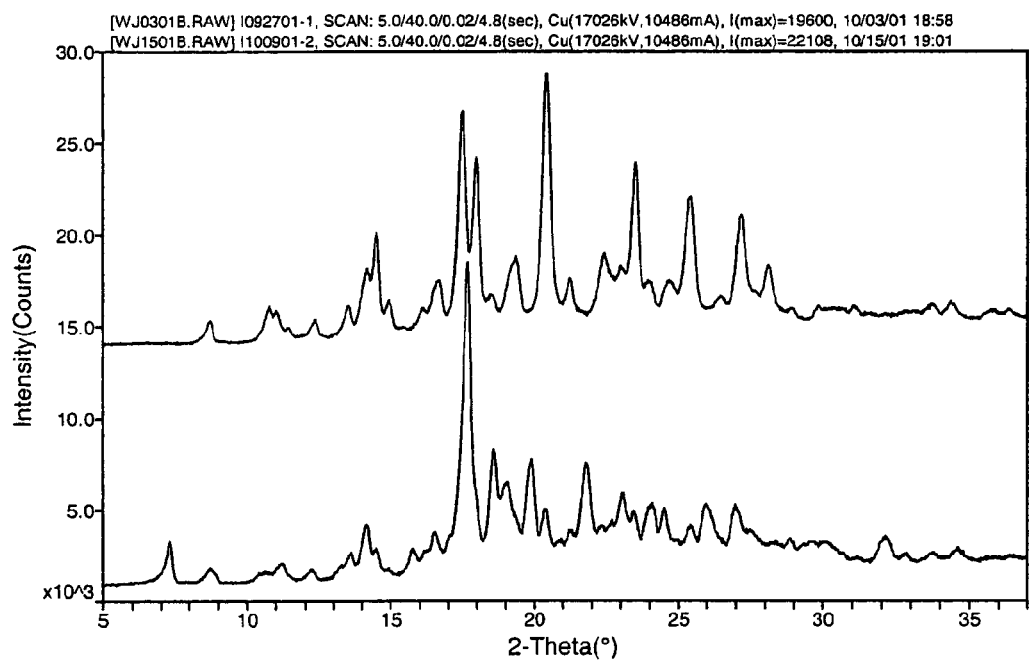

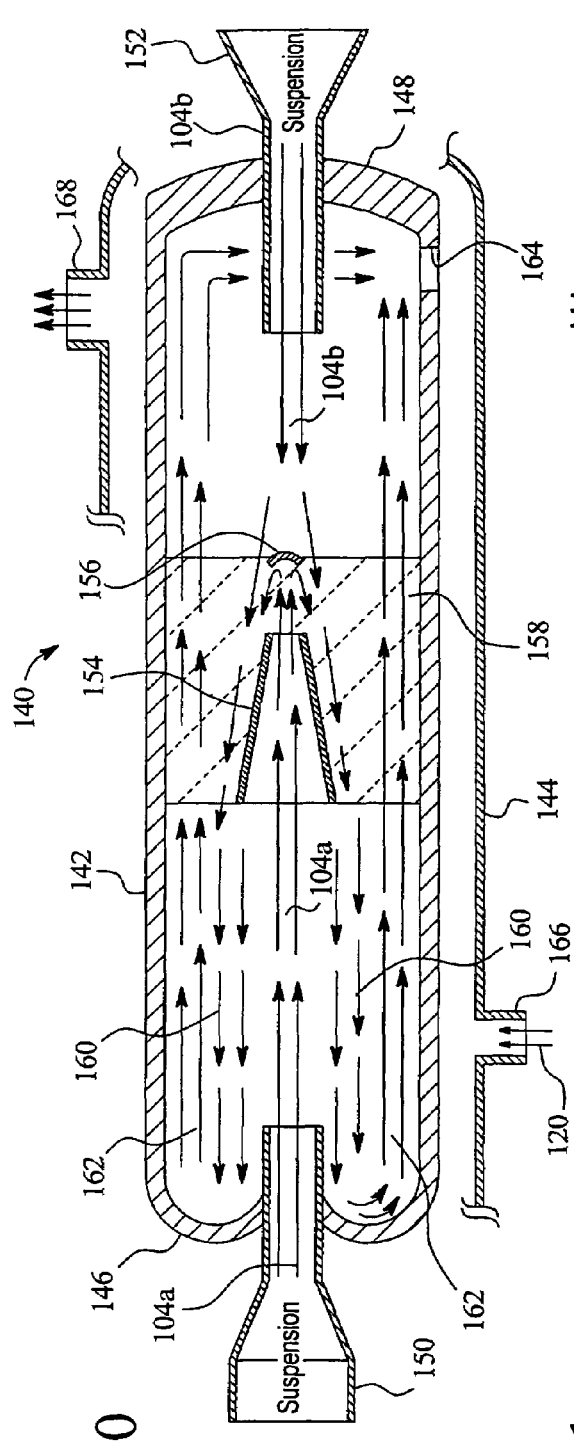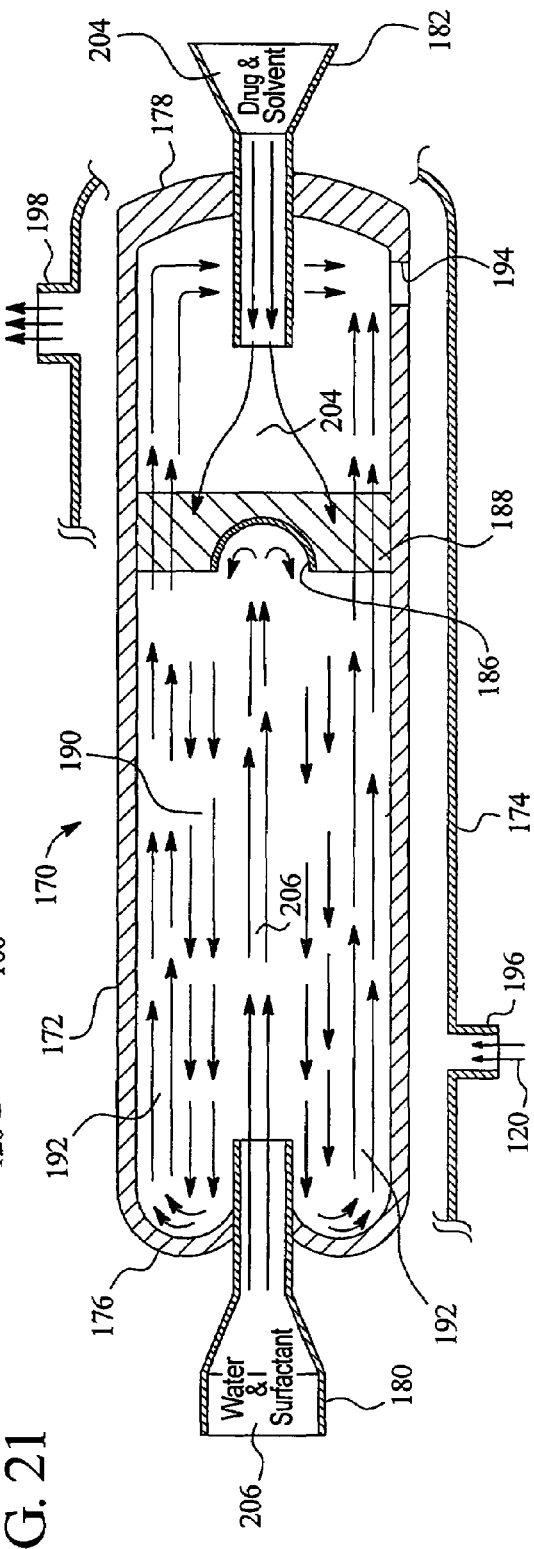

| Formulation | Itraconazole (%) | Pressure (psi) | Passes | Start Temp. (°C) | Final Temp. (°C) | Solutol HS15 (%) | Poloxamer 188 (%) | Phospholipids (%) | PH 7.5-8.5 | Glycerin (%) | TRIS (mM) | Nitrogen Sparge |
|---|---|---|---|---|---|---|---|---|---|---|---|---|
| A | 1 | 40,000 | Till Particle Size Plateaus Off | <10 | <70 | 0 | 0 | 1.2 | 8 | 2.2 | 5 | Yes |
| B | 1 | 40,000 | Till Particle Size Plateaus Off | <10 | <70 | 0 | 0.03 | 1.2 | 8 | 2.2 | 5 | Yes |
| C | 1 | 40,000 | Till Particle Size Plateaus Off | <10 | <70 | 0.75 | 0 | 0 | 8 | 2.2 | 5 | Yes |

METHODS AND APPARATUSES FOR THE COMMINUTION AND STABILIZATION OF SMALL PARTICLES

CROSS-REFERENCE TO RELATED APPLICATIONS

This application claims priority to provisional application Ser. No. 60/457,424 filed on Mar. 24, 2003, which is incorporated herein and made a part hereof in its entirety.

FEDERALLY SPONSORED RESEARCH OR DEVELOPMENT

Not Applicable.

BACKGROUND OF THE INVENTION

1. Technical Field

The present invention is concerned with the formation of small particles of organic compounds by precipitating the organic compounds in an aqueous medium to form a pre-suspension followed by adding energy to stabilize a coating of the particle or to alter the lattice structure of the particle. The present invention further contemplates simultaneously precipitating while adding energy. These processes are preferably used to prepare a suspension of small particles of a poorly water-soluble, pharmaceutically active compound suitable for in vivo delivery by an administrative route such as parenteral, oral, pulmonary, nasal, buccal, topical, ophthalmic, rectal, vaginal, transdermal or the like.

2. Background Art

There are an ever-increasing number of organic compounds being formulated for therapeutic or diagnostic effects that are poorly soluble or insoluble in aqueous solutions. Such drugs provide challenges to delivering them by the administrative routes detailed above. Compounds that are insoluble in water can have significant benefits when formulated as a stable suspension of sub-micron particles. Accurate control of particle size is essential for safe and efficacious use of these formulations. Particles must be less than seven microns in diameter to safely pass through capillaries without causing emboli (Allen et al., 1987; Davis and Taube, 1978; Schroeder et al., 1978; Yokel et al., 1981). One solution to this problem is the production of small particles of the insoluble drug candidate and the creation of a microparticulate or nanoparticulate suspension. In this way, drugs that were previously unable to be formulated in an aqueous based system can be made suitable for intravenous administration. Suitability for intravenous administration includes small particle size (<7 µm), low toxicity (as from toxic formulation components or residual solvents), and bioavailability of the drug particles after administration.

Preparations of small particles of water insoluble drugs may also be suitable for oral, pulmonary, topical, ophthalmic, nasal, buccal, rectal, vaginal, transdermal administration, or other routes of administration. The small size of the particles improves the dissolution rate of the drug, and hence improving its bioavailability and potentially its toxicity profiles. When administered by these routes, it may be desirable to have particle size in the range of 5 to 100 µm, depending on the route of administration, formulation, solubility, and bioavailability of the drug. For example, for oral administration, it is desirable to have a particle size of less than about 7 µm. For pulmonary administration, the particles are preferably less than about 10 µm in size.

SUMMARY OF THE INVENTION

The present invention provides a composition and a method for preparing a suspension of small particles of an organic compound, the solubility of which is greater in a water-miscible first solvent than in a second solvent that is aqueous. The process includes the steps of: (i) dissolving the organic compound in the water-miscible first solvent to form a solution; (ii) mixing the solution with the second solvent to define a pre-suspension of particles; and (iii) adding energy to the pre-suspension to form a suspension of particles having an average effective particle size of less than about 100 µm. In a preferred embodiment, the process further includes the step of mixing one or more surface modifiers into the first water-miscible solvent or the second solvent, or both the first water-miscible solvent and the second solvent.

The present invention further provides a method where the first and second steps of forming the presuspension are carried out simultaneously with the step of adding energy. This applies to all methods discussed herein.

The present invention also provides a composition and a method for preparing a suspension of small particles of a pharmaceutically active compound, the solubility of which is greater in a water-miscible first solvent than in a second solvent that is aqueous. The process includes the steps of: (i) dissolving the pharmaceutically active compound in the water-miscible first solvent to form a first solution; (ii) mixing the first solution with the second solvent to define a pre-suspension of particles; and (iii) adding energy to the pre-suspension to form a suspension of particles of the pharmaceutically active compound having an average effective particle size of less than about 100 µm. The water-miscible first solvent or the second solvent may optionally contain one or more surface modifiers. The composition can be delivered in vivo by an administrative route such as parenteral, oral, pulmonary, nasal, ophthalmic, topical, buccal, rectal, vaginal, transdermal or the like. In a preferred embodiment, the pharmaceutically active compound is poorly water-soluble. In another preferred embodiment, the process includes the additional step of sterilizing the composition.

The present invention still further provides a composition and a method of preparing a sterile pharmaceutical composition of small particles of a pharmaceutically active compound for parenteral administration. The solubility of the compound is greater in a water-miscible first solvent than in a second solvent that is aqueous. The process includes the steps of: (i) dissolving the pharmaceutically active compound in the water-miscible first solvent to form a first solution; (ii) mixing the first solution with the second solvent to define a pre-suspension of particles; (iii) adding energy to the pre-suspension to form a suspension of particles of the pharmaceutically active compound having an average effective particle size of less than about 7 µm; and (iv) sterilizing the composition. The water-miscible first solvent or the second solvent may optionally contain one or more surface modifiers. In a preferred embodiment, the pharmaceutically active compound is poorly water-soluble.

The present invention also provides a composition and method of preparing a pharmaceutical composition of small particles of a pharmaceutically active compound for oral delivery. The solubility of the compound is greater in a water-miscible first solvent than in a second solvent that is aqueous. The process includes the steps of: (i) dissolving the pharmaceutically active compound in the water-miscible first solvent to form a first solution; (ii) mixing the first solution with the second solvent to define a pre-suspension of particles; and (iii) adding energy to the pre-suspension to form a suspension of particles of the pharmaceutically active compound having an average effective particle size of less than about 100 μm. The water-miscible first solvent or the second solvent may optionally contain one or more surface modifiers. In a preferred embodiment, the pharmaceutically active compound is poorly water-soluble.

The present invention further provides a composition and method of preparing a pharmaceutical composition of small particles of a pharmaceutically active compound for pulmonary delivery. The solubility of the compound is greater in a water-miscible first solvent than in a second solvent that is aqueous. The process includes the steps of: (i) dissolving the pharmaceutically active compound in the water-miscible first solvent to form a first solution; (ii) mixing the first solution with the second solvent to define a pre-suspension of particles; and (iii) adding energy to the pre-suspension to form a suspension of particles of the pharmaceutically active compound having an average effective particle size of from less than about 10 μm. The water-miscible first solvent or the second solvent may optionally contain one or more surface modifiers. In a preferred embodiment, the pharmaceutically active compound is poorly water-soluble. The composition can be aerosolized and administered by a nebulizer. Alternatively, the process may include an additional step of removing the liquid phase from the suspension to form dry powder of the small particles. The dry powder can then be administered by a dry powder inhaler, or the dry powder can further be suspended in a hydrofluorocarbon propellant to be administered by a metered dose inhaler.

These and other aspects and attributes of the present invention will be discussed with reference to the following drawings and accompanying specification.

BRIEF DESCRIPTION OF THE DRAWINGS

FIG. 1 shows a diagrammatic representation of one method of the present invention;

FIG. 2 shows a diagrammatic representation of another method of the present invention;

FIG. 3 shows amorphous particles prior to homogenization;

FIG. 4 shows particles after annealing by homogenization;

FIG. 5 is an X-Ray diffractogram of microprecipitated itraconazole with polyethylene glycol-660 12-hydroxystearate before and after homogenization;

FIG. 6 shows Carbamazepine crystals before homogenization;

FIG. 7 shows Carbamazepine microparticulate after homogenization (Avestin C-50);

FIG. 8 is a diagram illustrating the Microprecipitation Process for Prednisolone;

FIG. 9 is a photomicrograph of prednisolone suspension before homogenization;

FIG. 10 is a photomicrograph of prednisolone suspension after homogenization;

FIG. 11 illustrates a comparison of size distributions of nanosuspensions (this invention) and a commercial fat emulsion;

FIG. 12 shows the X-ray powder diffraction patterns for raw material itraconazole (top) and SMP-2-PRE (bottom). The raw material pattern has been shifted upward for clarity;

FIG. 13*a* shows the DSC trace for raw material itraconazole;

FIG. 13*b* shows the DSC trace for SMP-2-PRE;

FIG. 14 illustrates the DSC trace for SMP-2-PRE showing the melt of the less stable polymorph upon heating to 160° C., a recrystallization event upon cooling, and the subsequent melting of the more stable polymorph upon reheating to 180° C.;

FIG. 15 illustrates a comparison of SMP-2-PRE samples after homogenization. Solid line=sample seeded with raw material itraconazole. Dashed line=unseeded sample. The solid line has been shifted by 1 W/g for clarity;

FIG. 16 illustrates the effect of seeding during precipitation. Dashed line =unseeded sample, solid line =sample seeded with raw material itraconazole. The unseeded trace (dashed line) has been shifted upward by 1.5 W/g for clarity; and FIG. 17 illustrates the effect of seeding the drug concentrate through aging. Top x-ray diffraction pattern is for crystals prepared from fresh drug concentrate, and is consistent with the stable polymorph (see FIG. 12, top). Bottom pattern is for crystals prepared from aged (seeded) drug concentrate, and is consistent with the metastable polymorph (see FIG. 12, bottom). The top pattern has been shifted upward for clarity.

FIG. 18 is a sectioned elevation view of one embodiment of an apparatus and method of the present invention for causing comminution of solid particles in a suspension.

FIG. 19 is a sectioned elevation view of one embodiment of an apparatus and method of the present invention for mixing components of a particle suspension to create the suspension and causing comminution of solid particles in the suspension.

FIG. 20 is a sectioned elevation view of one embodiment of an apparatus and method of the present invention for causing comminution of solid particles in a suspension using opposing fluid jet streams.

FIG. 21 is a sectioned elevation view of one embodiment of an apparatus and method of the present invention for mixing components of a particle suspension to create the suspension and causing comminution of solid particles in the suspension using opposing fluid jet streams.

FIG. 22 is a sectioned elevation view of one embodiment of a nozzle and method of using same of the present invention for causing high energy mixing and comminution of solid particles in a suspension.

FIG. 23 is a perspective view of one embodiment of a turbulating structure of the present invention that is inserted into the nozzle of FIG. 22.

FIG. 24 is a table showing various formulations of a solid drug processed via the apparatus and method of the present invention discussed in connection with claim 18.

FIG. 25 is a table comparing the results of the processing of the drug of FIG. 24 with results from a known method for processing solid particles in suspension.

DETAILED DESCRIPTION OF THE INVENTION

The present invention is susceptible of embodiments in many different forms. Preferred embodiments of the invention are disclosed with the understanding that the present disclosure is to be considered as exemplifications of the principles of the invention and are not intended to limit the broad aspects of the invention to the embodiments illustrated.

The present invention provides compositions and methods for forming small particles of an organic compound. An organic compound for use in the process of this invention is any organic chemical entity whose solubility decreases from one solvent to another. This organic compound might be a pharmaceutically active compound, which can be selected from therapeutic agents, diagnostic agents, cosmetics, nutritional supplements, and pesticides.

The therapeutic agents can be selected from a variety of known pharmaceuticals such as, but are not limited to: analgesics, anesthetics, analeptics, adrenergic agents, adrenergic blocking agents, adrenolytics, adrenocorticoids, adrenomimetics, anticholinergic agents, anticholinesterases, anticonvulsants, alkylating agents, alkaloids, allosteric inhibitors, anabolic steroids, anorexiants, antacids, antidiarrheals, antidotes, antifolics, antipyretics, antirheumatic agents, psychotherapeutic agents, neural blocking agents, anti-inflammatory agents, antihelmintics, anti-arrhythmic agents, antibiotics, anticoagulants, antidepressants, antidiabetic agents, antiepileptics, antifungals, antihistamines, antihypertensive agents, antimuscarinic agents, antimycobacterial agents, antimalarials, antiseptics, antineoplastic agents, antiprotozoal agents, immunosuppressants, immunostimulants, antithyroid agents, antiviral agents, anxiolytic sedatives, astringents, beta-adrenoceptor blocking agents, contrast media, corticosteroids, cough suppressants, diagnostic agents, diagnostic imaging agents, diuretics, dopaminergics, hemostatics, hematological agents, hemoglobin modifiers, hormones, hypnotics, immuriological agents, antihyperlipidemic and other lipid regulating agents, muscarinics, muscle relaxants, parasympathomimetics, parathyroid calcitonin, prostaglandins, radio-pharmaceuticals, sedatives, sex hormones, anti-allergic agents, stimulants, sympathomimetics, thyroid agents, vasodilators, vaccines, vitamins, and xanthines. Antineoplastic, or anticancer agents, include but are not limited to paclitaxel and derivative compounds, and other antineoplastics selected from the group consisting of alkaloids, antimetabolites, enzyme inhibitors, alkylating agents and antibiotics. The therapeutic agent can also be a biologic, which includes but is not limited to proteins, polypeptides, carbohydrates, polynucleotides, and nucleic acids. The protein can be an antibody, which can be polyclonal or monoclonal.

Diagnostic agents include the x-ray imaging agents and contrast media. Examples of x-ray imaging agents include WIN-8883 (ethyl 3,5-diacetamido-2,4,6-triiodobenzoate) also known as the ethyl ester of diatrazoic acid (EEDA), WIN 67722, i.e., (6-ethoxy-6-oxohexyl-3,5-bis(acetamido)-2,4,6-triiodobenzoate; ethyl-2-(3,5-bis(acetamido)-2,4,6-triiodobenzoyloxy) butyrate (WIN 16318); ethyl diatrizoxyacetate (WIN 12901); ethyl 2-(3,5-bis(acetamido)-2,4,6-triiodobenzoyloxy)propionate (WIN 16923); N-ethyl 2-(3,5-bis(acetamido)-2,4,6-triiodobenzoyloxy acetamide (WIN 65312); isopropyl 2-(3,5-bis(acetamido)-2,4,6-triiodobenzoyloxy) acetamide (WIN 12855); diethyl 2-(3,5-bis(acetamido)-2,4, 6-triiodobenzoyloxy malonate (WIN 67721); ethyl 2-(3,5-bis (acetamido)-2,4,6-triiodobenzoyloxy) phenylacetate (WIN 67585); propanedioic acid, [[3,5-bis(acetylamino)-2,4,5-triodobenzoyl]oxy]bis(1-methyl)ester (WIN 68165); and benzoic acid, 3,5-bis(acetylamino)-2,4,6-triodo-4-(ethyl-3-ethoxy-2-butenoate) ester (WIN 68209). Preferred contrast agents include those that are expected to disintegrate relatively rapidly under physiological conditions, thus minimizing any particle associated inflammatory response. Disintegration may result from enzymatic hydrolysis, solubilization of carboxylic acids at physiological pH, or other mechanisms. Thus, poorly soluble iodinated carboxylic acids such as iodipamide, diatrizoic acid, and metrizoic acid, along with hydrolytically labile iodinated species such as WIN 67721, WIN 12901, WIN 68165, and WIN 68209 or others may be preferred.

Other contrast media include, but are not limited to, particulate preparations of magnetic resonance imaging aids such as gadolinium chelates, or other paramagnetic contrast agents. Examples of such compounds are gadopentetate dimeglumine (Magnevist®) and gadoteridol (Prohance®).

A description of these classes of therapeutic agents and diagnostic agents and a listing of species within each class can be found in Martindale, The Extra Pharmacopoeia, Twenty-ninth Edition, The Pharmaceutical Press, London, 1989 which is incorporated herein by reference and made a part hereof. The therapeutic agents and diagnostic agents are commercially available and/or can be prepared by techniques known in the art.

A cosmetic agent is any active ingredient capable of having a cosmetic activity. Examples of these active ingredients can be, inter alia, emollients, humectants, free radical-inhibiting agents, anti-inflammatories, vitamins, depigmenting agents, anti-acne agents, antiseborrhoeics, keratolytics, slimming agents, skin coloring agents and sunscreen agents, and in particular linoleic acid, retinol, retinoic acid, ascorbic acid alkyl esters, polyunsaturated fatty acids, nicotinic esters, tocopherol nicotinate, unsaponifiables of rice, soybean or shea, ceramides, hydroxy acids such as glycolic acid, selenium derivatives, antioxidants, beta-carotene, gamma-orizanol and stearyl glycerate. The cosmetics are commercially available and/or can be prepared by techniques known in the art.

Examples of nutritional supplements contemplated for use in the practice of the present invention include, but are not limited to, proteins, carbohydrates, water-soluble vitamins (e.g., vitamin C, B-complex vitamins, and the like), fat-soluble vitamins (e.g., vitamins A, D, E, K, and the like), and herbal extracts. The nutritional supplements are commercially available and/or can be prepared by techniques known in the art.

The term pesticide is understood to encompass herbicides, insecticides, acaricides, nematicides, ectoparasiticides and fungicides. Examples of compound classes to which the pesticide in the present invention may belong include ureas, triazines, triazoles, carbamates, phosphoric acid esters, dinitroanilines, morpholines, acylalanines, pyrethroids, benzilic acid esters, diphenylethers and polycyclic halogenated hydrocarbons. Specific examples of pesticides in each of these classes are listed in Pesticide Manual, 9th Edition, British Crop Protection Council. The pesticides are commercially available and/or can be prepared by techniques known in the art.

Preferably the organic compound or the pharmaceutically active compound is poorly water-soluble. What is meant by "poorly water soluble" is a solubility of the compound in water of less than about 10 mg/mL, and preferably less than 1 mg/mL. These poorly water-soluble agents are most suitable for aqueous suspension preparations since there are limited alternatives of formulating these agents in an aqueous medium.

The present invention can also be practiced with water-soluble pharmaceutically active compounds, by entrapping these compounds in a solid carrier matrix (for example, poly-lactate-polyglycolate copolymer, albumin, starch), or by encapsulating these compounds in a surrounding vesicle that is impermeable to the pharmaceutical compound. This encapsulating vesicle can be a polymeric coating such as polyacrylate. Further, the small particles prepared from these water soluble pharmaceutical agents can be modified to improve chemical stability and control the pharmacokinetic properties of the agents by controlling the release of the agents from the particles. Examples of water-soluble pharmaceutical agents include, but are not limited to, simple organic compounds, proteins, peptides, nucleotides, oligonucleotides, and carbohydrates.

The particles of the present invention have an average effective particle size of generally less than about 100 μm as measured by dynamic light scattering methods, e.g., photo-correlation spectroscopy, laser diffraction, low-angle laser light scattering (LALLS), medium-angle laser light scattering (MALLS), light obscuration methods (Coulter method, for example), rheology, or microscopy (light or electron). However, the particles can be prepared in a wide range of sizes, such as from about 20 μm to about 10 nm, from about 10 μm to about 10 nm, from about 2 μm to about 10 nm, from about 1 μm to about 10 nm, from about 400 nm to about 50 nm, from about 200 nm to about 50 nm or any range or combination of ranges therein. The preferred average effective particle size depends on factors such as the intended route of administration, formulation, solubility, toxicity and bioavailability of the compound.

To be suitable for parenteral administration, the particles preferably have an average effective particle size of less than about 7 μm, and more preferably less than about 2 μm or any range or combination of ranges therein. Parenteral administration includes intravenous, intra-arterial, intrathecal, intraperitoneal, intraocular, intra-articular, intradural, intraventricular, intrapericardial, intramuscular, intradermal or subcutaneous injection.

Particles sizes for oral dosage forms can be in excess of 2 μm. The particles can range in size up to about 100 μm, provided that the particles have sufficient bioavailability and other characteristics of an oral dosage form. Oral dosage forms include tablets, capsules, caplets, soft and hard gel capsules, or other delivery vehicle for delivering a drug by oral administration.

The present invention is further suitable for providing particles of the organic compound in a form suitable for pulmonary administration. Particles sizes for pulmonary dosage forms can be in excess of 500 nm and typically less than about 10 μm. The particles in the suspension can be aerosolized and administered by a nebulizer for pulmonary administration. Alternatively, the particles can be administered as dry powder by a dry powder inhaler after removing the liquid phase from the suspension, or the dry powder can be resuspended in a non-aqueous propellant for administration by a metered dose inhaler. An example of a suitable propellant is a hydrofluorocarbon (HFC) such as HFC-134a (1,1,1,2-tetrafluoroethane) and HFC-227ea (1,1,1,2,3,3,3-heptafluoropropane). Unlike chlorofluorcarbons (CFC's), HFC's exhibit little or no ozone depletion potential.

Dosage forms for other routes of delivery, such as nasal, topical, ophthalmic, nasal, buccal, rectal, vaginal, transdermal and the like can also be formulated from the particles made from the present invention.

The processes for preparing the particles can be separated into four general categories. Each of the categories of processes share the steps of: (1) dissolving an organic compound in a water miscible first solvent to create a first solution, (2) mixing the first solution with a second solvent of water to precipitate the organic compound to create a pre-suspension, and (3) adding energy to the presuspension in the form of high-shear mixing or heat, or a combination of both, to provide a stable form of the organic compound having the desired size ranges defined above. The mixing steps and the adding energy step can be carried out in consecutive steps or simultaneously.

The categories of processes are distinguished based upon the physical properties of the organic compound as determined through x-ray diffraction studies, differential scanning calorimetry (DSC) studies, or other suitable study conducted prior to the energy-addition step and after the energy-addition step. In the first process category, prior to the energy-addition step the organic compound in the presuspension takes an amorphous form, a semi-crystalline form or a supercooled liquid form and has an average effective particle size. After the energy-addition step the organic compound is in a crystalline form having an average effective particle size essentially the same or less than that of the presuspension.

In the second process category, prior to the energy-addition step the organic compound is in a crystalline form and has an average effective particle size. After the energy-addition step the organic compound is in a crystalline form having essentially the same average effective particle size as prior to the energy-addition step but the crystals after the energy-addition step are less likely to aggregate.

The lower tendency of the organic compound to aggregate is observed by laser dynamic light scattering and light microscopy.

In the third process category, prior to the energy-addition step the organic compound is in a crystalline form that is friable and has an average effective particle size. What is meant by the term "friable" is that the particles are fragile and are more easily broken down into smaller particles. After the energy-addition step the organic compound is in a crystalline form having an average effective particle size smaller than the crystals of the pre-suspension. By taking the steps necessary to place the organic compound in a crystalline form that is friable, the subsequent energy-addition step can be carried out more quickly and efficiently when compared to an organic compound in a less friable crystalline morphology.

In the fourth process category, the first solution and second solvent are simultaneously subjected to the energy-addition step. Thus, the physical properties of the organic compound before and after the energy addition step were not measured.

The energy-addition step can be carried out in any fashion wherein the presuspension or the first solution and second solvent are exposed to cavitation, shearing or impact forces. In one preferred form of the invention, the energy-addition step is an annealing step. Annealing is defined in this invention as the process of converting matter that is thermodynamically unstable into a more stable form by single or repeated application of energy (direct heat or mechanical stress), followed by thermal relaxation. This lowering of energy may be achieved by conversion of the solid form from a less ordered to a more ordered lattice structure. Alternatively, this stabilization may occur by a reordering of the surfactant molecules at the solid-liquid interface.

These four process categories will be discussed separately below. It should be understood, however, that the process conditions such as choice of surfactants or combination of surfactants, amount of surfactant used, temperature of reaction, rate of mixing of solutions, rate of precipitation and the like can be selected to allow for any drug to be processed under any one of the categories discussed next.

The first process category, as well as the second, third, and fourth process categories, can be further divided into two subcategories, Method A and B, shown diagrammatically in FIGS. 1 and 2.

The first solvent according to the present invention is a solvent or mixture of solvents in which the organic compound of interest is relatively soluble and which is miscible with the second solvent. Such solvents include, but are not limited to water-miscible protic compounds, in which a hydrogen atom in the molecule is bound to an electronegative atom such as oxygen, nitrogen, or other Group VA, VIA and VII A in the Periodic Table of elements. Examples of such solvents include, but are not limited to, alcohols, amines (primary or secondary), oximes, hydroxamic acids, carboxylic acids, sulfonic acids, phosphonic acids, phosphoric acids, amides and ureas.

Other examples of the first solvent also include aprotic organic solvents. Some of these aprotic solvents can form hydrogen bonds with water, but can only act as proton acceptors because they lack effective proton donating groups. One class of aprotic solvents is a dipolar aprotic solvent, as defined by the International Union of Pure and Applied Chemistry (IUPAC Compendium of Chemical Terminology, 2nd Ed., 1997):

A solvent with a comparatively high relative permittivity (or dielectric constant), greater than ca. 15, and a sizable permanent dipole moment, that cannot donate suitably labile hydrogen atoms to form strong hydrogen bonds, e.g. dimethyl sulfoxide.

Dipolar aprotic solvents can be selected from the group consisting of: amides (fully substituted, with nitrogen lacking attached hydrogen atoms), ureas (fully substituted, with no hydrogen atoms attached to nitrogen), ethers, cyclic ethers, nitriles, ketones, sulfones, sulfoxides, fully substituted phosphates, phosphonate esters, phosphoramides, nitro compounds, and the like. Dimethylsulfoxide (DMSO), N-methyl-2-pyrrolidinone (NMP), 2-pyrrolidinone, 1,3-dimethylimidazolidinone (DMI), dimethylacetamide (DMA), dimethylformamide (DMF), dioxane, acetone, tetrahydrofuran (THF), tetramethylenesulfone (sulfolane), acetonitrile, and hexamethylphosphoramide (HMPA), nitromethane, among others, are members of this class.

Solvents may also be chosen that are generally water-immiscible, but have sufficient water solubility at low volumes (less than 10%) to act as a water-miscible first solvent at these reduced volumes. Examples include aromatic hydrocarbons, alkenes, alkanes, and halogenated aromatics, halogenated alkenes and halogenated alkanes. Aromatics include, but are not limited to, benzene (substituted or unsubstituted), and monocyclic or polycyclic arenes. Examples of substituted benzenes include, but are not limited to, xylenes (ortho, meta, or para), and toluene. Examples of alkanes include but are not limited to hexane, neopentane, heptane, isooctane, and cyclohexane. Examples of halogenated aromatics include, but are not restricted to, chlorobenzene, bromobenzene, and chlorotoluene. Examples of halogenated alkanes and alkenes include, but are not restricted to, trichloroethane, methylene chloride, ethylenedichloride (EDC), and the like.

Examples of the all of the above solvent classes include but are not limited to: N-methyl-2-pyrrolidinone (also called N-methyl-2-pyrrolidone), 2-pyrrolidinone (also called 2-pyrrolidone), 1,3-dimethyl-2-imidazolidinone (DMI), dimethylsulfoxide, dimethylacetamide, acetic acid, lactic acid, methanol, ethanol, isopropanol, 3-pentanol, n-propanol, benzyl alcohol, glycerol, butylene glycol (butanediol), ethylene glycol, propylene glycol, mono- and diacylated monoglycerides (such as glyceryl caprylate), dimethyl isosorbide, acetone, dimethylsulfone, dimethylformamide, 1,4-dioxane, tetramethylenesulfone (sulfolane), acetonitrile, nitromethane, tetramethylurea, hexamethylphosphoramide (HMPA), tetrahydrofuran (THF), dioxane, diethylether, tert-butylmethyl ether (TBME), aromatic hydrocarbons, alkenes, alkanes, halogenated aromatics, halogenated alkenes, halogenated alkanes, xylene, toluene, benzene, substituted benzene, ethyl acetate, methyl acetate, butyl acetate, chlorobenzene, bromobenzene, chlorotoluene, trichloroethane, methylene chloride, ethylenedichloride (EDC), hexane, neopentane, heptane, isooctane, cyclohexane, polyethylene glycol (PEG, for example, PEG-4, PEG-8, PEG-9, PEG-12, PEG-14, PEG-16, PEG-120, PEG-75, PEG-150), polyethylene glycol esters (examples such as PEG-4 dilaurate, PEG-20 dilaurate, PEG-6 isostearate, PEG-8 palmitostearate, PEG-150 palmitostearate), polyethylene glycol sorbitans (such as PEG-20 sorbitan isostearate), polyethylene glycol monoalkyl ethers (examples such as PEG-3 dimethyl ether, PEG-4 dimethyl ether), polypropylene glycol (PPG), polypropylene alginate, PPG-10 butanediol, PPG-10 methyl glucose ether, PPG-20 methyl glucose ether, PPG-15 stearyl ether, propylene glycol dicaprylate/dicaprate, propylene glycol laurate, and glycofurol (tetrahydrofurfuryl alcohol polyethylene glycol ether). A preferred first solvent is N-methyl-2-pyrrolidinone. Another preferred first solvent is lactic acid.

The second solvent is an aqueous solvent. This aqueous solvent may be water by itself. This solvent may also contain buffers, salts, surfactant(s), water-soluble polymers, and combinations of these excipients.

Method A

In Method A (see FIG. 1), the organic compound ("drug") is first dissolved in the first solvent to create a first solution. The organic compound can be added from about 0.1% (w/v) to about 50% (w/v) depending on the solubility of the organic compound in the first solvent. Heating of the concentrate from about 30° C. to about 100° C. may be necessary to ensure total dissolution of the compound in the first solvent.

A second aqueous solvent is provided with one or more optional surface modifiers such as an anionic surfactant, a cationic surfactant, a nonionic surfactant or a biologically surface active molecule added thereto. Suitable anionic surfactants include but are not limited to alkyl sulfonates, alkyl phosphates, alkyl phosphonates, potassium laurate, triethanolamine stearate, sodium lauryl sulfate, sodium dodecylsulfate, alkyl polyoxyethylene sulfates, sodium alginate, dioctyl sodium sulfosuccinate, phosphatidyl choline, phosphatidyl glycerol, phosphatidyl inosine, phosphatidylserine, phosphatidic acid and their salts, glyceryl esters, sodium carboxymethylcellulose, cholic acid and other bile acids (e.g., cholic acid, deoxycholic acid, glycocholic acid, taurocholic acid, glycodeoxycholic acid) and salts thereof (e.g., sodium deoxycholate, etc.). Suitable cationic surfactants include but are not limited to quaternary ammonium compounds, such as benzalkonium chloride, cetyltrimethylammonium bromide, chitosans, lauryldimethylbenzylammonium chloride, acyl camitine hydrochlorides, or alkyl pyridinium halides. As anionic surfactants, phospholipids may be used. Suitable phospholipids include, for example phosphatidylcholine, phosphatidylethanolamine, diacyl-glycero-phosphoethanolamine (such as dimyristoyl-glycero-phosphoethanolamine (DMPE), dipalmitoyl-glycero-phosphoethanolamine (DPPE), distearoyl-glycero-phosphoethanolamine (DSPE), and dioleolyl-glycero-phosphoethanolamine (DOPE)), phosphatidylserine, phosphatidylinositol, phosphatidylglycerol, phosphatidic acid, lysophospholipids, egg or soybean phospholipid or a combination thereof. The phospholipid may be salted or desalted, hydrogenated or partially hydrogenated or natural semisynthetic or synthetic. The phospholipid may also be conjugated with a water-soluble or hydrophilic polymer. A preferred polymer is polyethylene glycol (PEG), which is also known as the monomethoxy polyethyleneglycol (mPEG). The molecule weights of the PEG can vary, for example, from 200 to 50,000. Some commonly used PEG's that are commercially available include PEG 350, PEG 550, PEG 750, PEG 1000, PEG 2000, PEG 3000, and PEG 5000. The phospholipid or the PEG-phospholipid conjugate may also incorporate a functional group which can covalently attach to a ligand including but not limited to proteins, peptides, carbohydrates, glycoproteins, antibodies, or pharmaceutically active agents. These functional groups may conjugate with the ligands through, for example, amide bond formation, disulfide or thioether formation, or biotin/streptavidin binding. Examples of the ligand-binding functional groups include but are not limited to hexanoylamine, dodecanylamine, 1,12-dodecanedicarboxylate, thioethanol, 4-(p-maleimidophenyl)butyramide (MPB), 4-(p-maleimidomethyl)cyclohexane-carboxamide (MCC), 3-(2-pyridyldithio) propionate (PDP), succinate, glutarate, dodecanoate, and biotin.

Suitable nonionic surfactants include: polyoxyethylene fatty alcohol ethers (Macrogol and Brij), polyoxyethylene sorbitan fatty acid esters (Polysorbates), polyoxyethylene fatty acid esters (Myrj), sorbitan esters (Span), glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers (poloxamers), poloxamines, methylcellulose, hydroxymethylcellulose, hydroxypropylcellulose, hydroxypropylmethylcellulose, noncrystalline cellulose, polysaccharides including starch and starch derivatives such as hydroxyethylstarch (HES), polyvinyl alcohol, and polyvinylpyrrolidone. In a preferred form of the invention, the nonionic surfactant is a polyoxyethylene and polyoxypropylene copolymer and preferably a block copolymer of propylene glycol and ethylene glycol. Such polymers are sold under the tradename POLOXAMER also sometimes referred to as PLURONIC®, and sold by several suppliers including Spectrum Chemical and Ruger. Among polyoxyethylene fatty acid esters is included those having short alkyl chains. One example of such a surfactant is SOLUTOL® HS 15, polyethylene-660-hydroxystearate, manufactured by BASF Aktiengesellschaft.

Surface-active biological molecules include such molecules as albumin, casein, hirudin or other appropriate proteins. Polysaccharide biologics are also included, and consist of but not limited to, starches, heparin and chitosans.

It may also be desirable to add a pH adjusting agent to the second solvent such as sodium hydroxide, hydrochloric acid, tris buffer or citrate, acetate, lactate, meglumine, or the like. The second solvent should have a pH within the range of from about 3 to about 11.

For oral dosage forms one or more of the following excipients may be utilized: gelatin, casein, lecithin (phosphatides), gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens™, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethylcellulose phthalate, noncrystalline cellulose, magnesium aluminum silicate, triethanolamine, polyvinyl alcohol (PVA), and polyvinylpyrrolidone (PVP). Most of these excipients are described in detail in the Handbook of Pharmaceutical Excipients, published jointly by the American Pharmaceutical Association and The Pharmaceutical Society of Great Britain, the Pharmaceutical Press, 1986. The surface modifiers are commercially available and/or can be prepared by techniques known in the art. Two or more surface modifiers can be used in combination.

In a preferred form of the invention, the method for preparing small particles of an organic compound includes the steps of adding the first solution to the second solvent. The addition rate is dependent on the batch size, and precipitation kinetics for the organic compound. Typically, for a small-scale laboratory process (preparation of 1 liter), the addition rate is from about 0.05 cc per minute to about 10 cc per minute. During the addition, the solutions should be under constant agitation. It has been observed using light microscopy that amorphous particles, semi-crystalline solids, or a supercooled liquid are formed to create a pre-suspension. The method further includes the step of subjecting the pre-suspension to an energy-addition step to convert the amorphous particles, supercooled liquid or semicrystalline solid to a more stable, crystalline solid state. The resulting particles will have an average effective particles size as measured by dynamic light scattering methods (e.g., photocorrelation spectroscopy, laser diffraction, low-angle laser light scattering (LALLS), medium-angle laser light scattering (MALLS), light obscuration methods (Coulter method, for example), rheology, or microscopy (light or electron) within the ranges set forth above). In process category four, the first solution and the second solvent are combined while simultaneously conducting the energy-addition step.

The energy-addition step involves adding energy through sonication, homogenization, countercurrent flow homogenization, microfluidization, or other methods of providing impact, shear or cavitation forces. The same may be cooled or heated during this stage. In one preferred form of the invention, the energy-addition step is affected by a piston gap homogenizer such as the one sold by Avestin Inc. under the product designation EMULSIFLEX®-C160. In another preferred form of the invention, the energy-addition step may be accomplished by ultrasonication using an ultrasonic processor such as the Vibra-Cell Ultrasonic Processor (600W), manufactured by Sonics and Materials, Inc. In yet another preferred form the invention, the energy-addition step may be accomplished by use of an emulsification apparatus as described in U.S. Pat. No. 5,720,551 which is incorporated herein by reference and made a part hereof.

Depending upon the rate of energy addition, it may be desirable to adjust the temperature of the processed sample to within the range of from approximately −30° C. to 30° C. Alternatively, in order to effect a desired phase change in the processed solid, it may also be necessary to heat the pre-suspension to a temperature within the range of from about 30° C. to about 100° C. during the energy-addition step.

Method B

Method B differs from Method A in the following respects. The first difference is a surfactant or combination of surfactants is added to the first solution. The surfactants may be selected from the groups of anionic, nonionic, cationic surfactants, and surface-active biological modifiers set forth above.

Comparative Example of Method A and Method B and U.S. Pat. No. 5,780,062

U.S. Pat. No. 5,780,062 discloses a process for preparing small particles of an organic compound by first dissolving the compound in a suitable water-miscible first solvent. A second solution is prepared by dissolving a polymer and an amphiphile in aqueous solvent. The first solution is then added to the second solution to form a precipitate that consists of the organic compound and a polymer-amphiphile complex. The '062 Patent does not disclose utilizing the energy-addition step of this invention in Methods A and B. Lack of stability is typically evidenced by rapid aggregation and particle growth. In some instances, amorphous particles recrystallize as large crystals. Adding energy to the pre-suspension in the manner disclosed above typically affords particles that show decreased rates of particle aggregation and growth, as well as the absence of recrystallization upon product storage.

Methods A and B are further distinguished from the process of the '062 patent by the absence of a step of forming a polymer-amphiphile complex prior to precipitation. In Method A, such a complex cannot be formed as no polymer is added to the diluent (aqueous) phase. In Method B, the surfactant, which may also act as an amphiphile, or polymer, is dissolved with the organic compound in the first solvent. This precludes the formation of any amphiphile-polymer complexes prior to precipitation. In the '062 Patent, successful precipitation of small particles relies upon the formation of an amphiphile-polymer complex prior to precipitation. The '062 Patent discloses the amphiphile-polymer complex forms aggregates in the aqueous second solution. The '062 Patent explains the hydrophobic organic compound interacts with the amphiphile-polymer complex, thereby reducing solubility of these aggregates and causing precipitation. In the present invention, it has been demonstrated that the inclusion of the surfactant or polymer in the first solvent (Method B) leads, upon subsequent addition to second solvent, to formation of a more uniform, finer particulate than is afforded by the process outlined by the '062 Patent.

To this end, two formulations were prepared and analyzed. Each of the formulations has two solutions, a concentrate and an aqueous diluent, which are mixed together and then sonicated. The concentrate in each formulation has an organic compound (itraconazole), a water miscible solvent (N-methyl-2-pyrrolidinone or NMP) and possibly a polymer (poloxamer 188). The aqueous diluent has water, a tris buffer and possibly a polymer (poloxamer 188) and/or a surfactant (sodium deoxycholate). The average particle diameter of the organic particle is measured prior to sonication and after sonication.

The first formulation A has as the concentrate itraconazole and NMP. The aqueous diluent includes water, poloxamer 188, tris buffer and sodium deoxycholate. Thus the aqueous diluent includes a polymer (poloxamer 188), and an amphiphile (sodium deoxycholate), which may form a polymer/amphiphile complex, and, therefore, is in accordance with the disclosure of the '062 Patent. (However, again the '062 Patent does not disclose an energy addition step.) The second formulation B has as the concentrate itraconazole, NMP and poloxamer 188. The aqueous diluent includes water, tris buffer and sodium deoxycholate. This formulation is made in accordance with the present invention. Since the aqueous diluent does not contain a combination of a polymer (poloxamer) and an amphiphile (sodium deoxycholate), a polymer/amphiphile complex cannot form prior to the mixing step.

Table 1 shows the average particle diameters measured by laser diffraction on three replicate suspension preparations. An initial size determination was made, after which the sample was sonicated for 1 minute. The size determination was then repeated. The large size reduction upon sonication of Method A was indicative of particle aggregation.

TABLE 1

| Method | Concentrate | Aqueous Diluent | Average particle diameter (microns) | After sonication (1 minute) |
|---|---|---|---|---|
| A | itraconazole, (18%) N-methyl-2-pyrrolidinone (6 mL) | poloxamer 188 (2.3%), sodium deoxycholate (0.3%) tris buffer (5 mM, pH 8) | 18.7<br>10.7<br>12.1 | 2.36<br>2.46<br>1.93 |

TABLE 1-continued

| Method | Concentrate | Aqueous Diluent | Average particle diameter (microns) | After sonication (1 minute) |
|---|---|---|---|---|
| B | itraconazole (18%)poloxamer 188 (37%)N-methyl-2-pyrrolidinone (6 mL) | water (qs to 94 mL) sodium deoxycholate (0.3%)tris buffer (5 mM, pH 8) water (qs to 94 mL) | 0.194<br>0.178<br>0.181 | 0.198<br>0.179<br>0.177 |

A drug suspension resulting from application of the processes described in this invention may be administered directly as an injectable solution, provided Water for Injection is used in formulation and an appropriate means for solution sterilization is applied. Sterilization may be accomplished by methods well known in the art such as steam or heat sterilization, gamma irradiation and the like. Other sterilization methods, especially for particles in which greater than 99% of the particles are less than 200 nm, would also include pre-filtration first through a 3.0 micron filter followed by filtration through a 0.45-micron particle filter, followed by steam or heat sterilization or sterile filtration through two redundant 0.2-micron membrane filters. Yet another means of sterilization is sterile filtration of the concentrate prepared from the first solvent containing drug and optional surfactant or surfactants and sterile filtration of the aqueous diluent. These are then combined in a sterile mixing container, preferably in an isolated, sterile environment. Mixing, homogenization, and further processing of the suspension are then carried out under aseptic conditions.

Yet another procedure for sterilization would consist of heat sterilization or autoclaving within the homogenizer itself, before, during, or subsequent to the homogenization step. Processing after this heat treatment would be carried out under aseptic conditions.

Optionally, a solvent-free suspension may be produced by solvent removal after precipitation. This can be accomplished by centrifugation, dialysis, diafiltration, force-field fractionation, high-pressure filtration, reverse osmosis, or other separation techniques well known in the art. Complete removal of N-methyl-2-pyrrolidinone was typically carried out by one to three successive centrifugation runs; after each centrifugation (18,000 rpm for 30 minutes) the supernatant was decanted and discarded. A fresh volume of the suspension vehicle without the organic solvent was added to the remaining solids and the mixture was dispersed by homogenization. It will be recognized by those skilled in the art that other high-shear mixing techniques could be applied in this reconstitution step. Alternatively, the solvent-free particles can be formulated into various dosage forms as desired for a variety of administrative routes, such as oral, pulmonary, nasal, topical, intramuscular, and the like.

Furthermore, any undesired excipients such as surfactants may be replaced by a more desirable excipient by use of the separation methods described in the above paragraph. The solvent and first excipient may be discarded with the supernatant after centrifugation or filtration. A fresh volume of the suspension vehicle without the solvent and without the first excipient may then be added. Alternatively, a new surfactant may be added. For example, a suspension consisting of drug, N-methyl-2-pyrrolidinone (solvent), poloxamer 188 (first excipient), sodium deoxycholate, glycerol and water may be replaced with phospholipids (new surfactant), glycerol and water after centrifugation and removal of the supernatant.

I. First Process Category

The methods of the first process category generally include the step of dissolving the organic compound in a water miscible first solvent followed by the step of mixing this solution with an aqueous solvent to form a presuspension wherein the organic compound is in an amorphous form, a semicrystalline form or in a supercooled liquid form as determined by x-ray diffraction studies, DSC, light microscopy or other analytical techniques and has an average effective particle size within one of the effective particle size ranges set forth above. The mixing step is followed by an energy-addition step.

II. Second Process Category

The methods of the second processes category include essentially the same steps as in the steps of the first processes category but differ in the following respect. An x-ray diffraction, DSC or other suitable analytical techniques of the presuspension shows the organic compound in a crystalline form and having an average effective particle size. The organic compound after the energy-addition step has essentially the same average effective particle size as prior to the energy-addition step but has less of a tendency to aggregate into larger particles when compared to that of the particles of the presuspension. Without being bound to a theory, it is believed the differences in the particle stability may be due to a reordering of the surfactant molecules at the solid-liquid interface.

III. Third Process Category

The methods of the third category modify the first two steps of those of the first and second processes categories to ensure the organic compound in the presuspension is in a friable form having an average effective particle size (e.g., such as slender needles and thin plates). Friable particles can be formed by selecting suitable solvents, surfactants or combination of surfactants, the temperature of the individual solutions, the rate of mixing and rate of precipitation and the like. Friability may also be enhanced by the introduction of lattice defects (e.g., cleavage planes) during the steps of mixing the first solution with the aqueous solvent. This would arise by rapid crystallization such as that afforded in the precipitation step. In the energy-addition step these friable crystals are converted to crystals that are kinetically stabilized and having an average effective particle size smaller than those of the presuspension. Kinetically stabilized means particles have a reduced tendency to aggregate when compared to particles that are not kinetically stabilized. In such instance the energy-addition step results in a breaking up of the friable particles. By ensuring the particles of the presuspension are in a friable state, the organic compound can more easily and more quickly be prepared into a particle within the desired size ranges when compared to processing an organic compound where the steps have not been taken to render it in a friable form.

IV. Fourth Process Category

The methods of the fourth process category include the steps of the first process category except that the mixing step is carried out simultaneously with the energy-addition step.

Comminuting and Stabilizing of Small Particles

As discussed above, one preferred annealing process can be accomplished using the apparatus described in U.S. Pat. No. 5,720,551 ("the '551 Patent"). The '551 Patent describes a method and apparatus for creating an emulsion of two immiscible liquid phases. One phase is an oil phase, wherein liquid droplets or solid particles are dissolved in oil or some other fluid that is insoluble in water. The other liquid phase of the '551 Patent is described as a an aqueous phase. The oil and aqueous liquid phases are mixed and fed through an emulsifying cell. The emulsifying cell creates opposing fluid streams. The opposing fluid streams create shear forces, impact forces and cavitation forces. Those forces aid in comminution of the oil phase and provide the mixing necessary to coat any new uncoated product surfaces created by the comminution.

The emulsification process discussed in the '551 Patent involves the breakdown of the oil phase into smaller more uniform droplets, wherein an emulsifier interacts with the smaller droplets to form the emulsion. The '551 Patent describes the breakdown of a liquid within a liquid, i.e., the oil phase within the aqueous phase. That patent does not teach the breakdown of solid particles that are relatively or completely insoluble in water.

There are methods for breaking down solid or crystalline structures into smaller particles. One procedure for comminuting particles is disclosed in U.S. Pat. No. 5,314,506, the teachings of which are incorporated herein by reference and made a part hereof. That patent discloses the orientation of fluid jet streams toward one another to create high impact forces. The patent is particularly directed to using the high impact forces for micro-mixing in situations where no chemical reaction is involved.

The inventors of the present invention have discovered that relying solely on impact forces to create the micron and sub-micron sized drug particles of the present invention causes a number of problems. For example, it has been determined that at least twenty passes at 20,000 pounds per square inch ("psig") through a piston-gap homogenizer was required to achieve a mean particle size below one micron. Such repeated use of the piston-gap homogenizer leads to wear on the bearings and seals of the homogenizer, requiring frequent replacement of those items.

It is believed that the teachings of the present invention solve the problems associated with breaking down and stabilizing small particles of organic compounds in an aqueous medium via the application of a high shear counter-current flow regime. As alluded to above, that regime results in a plurality of different forces acting on the particles to cause cleavage or splitting of the solid particles into smaller particles. In particular, the shearing regime results in shear forces, impact forces and cavitation. One or more optional surfactants can be provided in the bulk fluid carrying the particles so that when cleavage or splitting occurs leaving uncoated surfaces, the surfactant immediately coats such surfaces, yielding a smaller, stable particle.

Cavitation in the devices illustrated in FIGS. 18 to 22 occurs when a sudden acceleration occurs within those devices, coinciding with a sudden pressure drop, to cause the local pressure in the fluid surrounding the particles (water and surfactants) to drop momentarily below the vapor pressure of such surrounding fluid. The drop in vapor pressure causes small vapor bubbles to form. One theory holds that when those bubbles collapse, shock waves in the fluid are created that break down or crack the solid, organic particles.

The differential velocities of opposing fluid streams cause shearing to occur within the chambers of the devices of FIGS. 18 to 21. Generally, a velocity of the fluid and particles in the center of the chamber is much higher than the velocity of the fluid traveling in a substantially opposite direction near the interior surface of the chamber (such velocity tending towards zero). The shearing results in shear forces, impact forces as well as cavitation forces as described above.

In general, the apparatuses of FIGS. 18 to 21 cause the solid particles in fluid suspension to travel in a first fluid stream and in a first direction until reaching an obstruction placed in front of the first stream. The obstruction redirects the suspension to flow in a second stream and in a second direction. The second stream and direction are positioned and oriented with respect to the first stream and direction to cause shear and cavitation between the first and second fluid streams. In one embodiment, the first and second directions are directly opposite or substantially opposite to one another.

Referring now to FIG. 18, one embodiment for breaking down solid or crystalline particles into smaller of such particles is illustrated by apparatus 100. In apparatus 100, solid particles in a suspension fluid, such as water and surfactants describe herein, are forced through at least one jet generating orifice 102 and into cavity 110, wherein the kinetic energy of the fluid jet 104 is absorbed by a fluid stream 106 flowing around and in the opposite direction of jet 104. The oppositely flowing streams 104 and 106 create intense forces due to shear, impact, and cavitation, further breaking down and mixing the solid particles to create stable, micron, sub-micron or nano-sized particles. The surfactants described herein are configured such that they readily flow to contact the comminuted particles to stabilize same.

Fluid jet 104 remains relatively unchanged when it flows into an opening 108 of apparatus 100. Jet 104 flows from opening 108 into the cavity 110. Cavity 110 is defined by a cylindrical annular wall and a semi-spherical impacting surface 112. In an alternative embodiment, semi-spherical surface 112 is flat or shaped otherwise. When the fluid stream 104 impacts surface 112, the fluid reverses flow and forms a second coherent annular counter-flow stream 106.

Because the only way out of cavity 110 is to reverse direction, annular counter-flow stream 106 is formed. Counter-flow stream 106 is therefore forced to interact with incoming jet 104. In doing so, counter-flow stream 106 absorbs the kinetic energy of the fluid jet 104, generating the intense interactive forces.

The exchange of kinetic energy causes the temperature of the fluid surrounding the particles to increase. The increase in temperature is potentially harmful to certain components of the suspension fluid stream 104. It may therefore be desirable to cool the outgoing fluid and comminuted, stabilized particles immediately after such particles are comminuted and stabilized. Accordingly, after exiting cavity 110, the stabilized product flows between surfaces 114 and 116 and through outlet opening 118. A cooling fluid 120 is provided through an opening 122. Cooling fluid 120 contacts the stabilized product exiting the opening 118. The cooling fluid 120 interacts with the warm product, cooling the product and further mixing same.

The generally counter flow nature of the cooling fluid 120 and the exiting stabilized product is a very efficient method of heat exchange. Cooling fluid 120 is cool water in one embodiment. In another embodiment, cool air or vaporized nitrogen or carbon dioxide is used. The cooled fluid containing the comminuted and stabilized particles exits through annular opening 124 of apparatus 100.

In the embodiment illustrated in connection with FIG. 18, at least some of if not much of the breaking down and comminuting of the solid particles occurs in the creation of the fluid jet through orifice 102. The shear forces created by counter flowing streams 104 and 106 serve further to break down the components as well as to mix the comminuted components with the surfactant coating materials or to stabilize the interface between the surfactant and the drug particle.

FIG. 18 shows that the jet or fluid stream 104 is a suspension formed by either method A or method B described above. That is, the chemical reaction that takes place to create the suspension has already occurred at some point prior to the suspension flowing through orifice 102 to create jet 104.

Referring now to FIG. 19, an alternative apparatus 130 mixes the water miscible organic solvent and drug with the aqueous solution to precipitate the drug particles as well as perform the functions described above in connection with apparatus 100 of FIG. 18. Apparatus 130 includes many of the same components as described above, such as an orifice 102 that creates a jet of fluid 204. Fluid jet 204 differs from jet 104 in that jet 204 includes the components of the drug and water miscible organic solvent disclosed by method A of FIG. 1 or the drug, solvent or one or more surfactants discussed above in connection with method B of FIG. 2 prior to mixing of the components.

Apparatus 130 takes advantage of the Venturi pump effect by placing a suction tube 126 in front of the restricted orifice 102 leading to cavity 110. The drop in pressure and increase in velocity created by nozzle 102 creates a suction force in tube 126. Such negative force pulls the water and optional surfactants through the suction tube 126 and into stream 204 to create the suspension stream 104 discussed above. The high energy area within orifice 102 mixes the drug, water miscible organic solvent and optional surfactant solution with the water and optional surfactant solution, yielding one of the particle suspensions as described herein. The drop in pressure and increase in velocity created by nozzle 102 also causes cavitation and much of the comminution of the solid particles. The apparatus 130 eliminates the premixing step associated with the apparatus 100 of FIG. 18 and allows one device to mix, precipitate, comminute, anneal or otherwise form a stable particle suspension as defined above.

The comminuted particles may not have enough time to be fully stabilized in the nozzle 102. Therefore, once the mixing takes place via the Venturi pump suctioning of the aqueous medium and optional surfactant solution 206 into the drug, water-miscible organic solvent and optional surfactant stream 204, and the particles precipitate and are comminuted in or adjacent the nozzle 102, the jet stream 104 flows through opening 108, into cavity 110 and impacts surface 112. A second fluid stream 106 flows opposite to stream 104, creating shear forces, impact forces and further cavitation of the suspension. That shearing further breaks down the particles and mixes the particles with the fluid to coat the particles or to stabilize the coating on the particle. As above, the stabilized fluid exits opening 118, where it meets a counter flow of cooling fluid or gas 120, which enters via opening 122. The cooled and stabilized suspension exits apparatus 130 via annular opening 124.

FIG. 19 illustrates the water and optional surfactants 206 being sucked via tube 126 into a stream containing drug and solvent 204. It should be appreciated that the reverse is also possible, wherein the drug and solvent 204 are sucked via tube 126 into the water and surfactant stream 206.

FIGS. 18 and 19 illustrate embodiments having a single fluid inlet (the Venturi embodiment of FIG. 19 ultimately includes a single stream 104 flowing through orifice 102). Referring now to FIGS. 20 and 21, various embodiments are illustrated which include multiple inlets. That is, there are two entrance points for either the premixed suspension 104 or the constituent components thereof. Apparatus 140 of FIG. 20 is illustrated showing suspensions 104*a* and 104*b* (collectively referred to as suspension 104) that are injected at separate points within apparatus 140. FIG. 21 illustrates that the water and optional surfactant 206 are injected into one end of apparatus 170, while the drug and solvent 204 are injected on the other side of apparatus 170.

It should be appreciated that the fluid regimes of FIGS. 20 and 21 are not limited to the illustrated inlet configurations and may alternatively include the configuration of the other apparatus or a different inlet configuration altogether. For example, in either apparatus 140 or 170, the suspension 104 can be injected through one inlet, while a separate fluid designed specifically for mixing the suspension, or alternatively for cooling the suspension, is injected in the other inlet.

Apparatus 140 of FIG. 20 includes an inner shell 142 and an outer shell 144. Inner shell 142 includes end caps 146 and 148. Nozzle 150 is welded to end cap 146, while nozzle 152 is welded to end cap 148.

Positioned somewhere inside inner shell 142 is a nozzle 154 and an impingement surface 156. In one embodiment, nozzle 154 and impingement surface 156 are welded to one or more thin (e.g., metal) plates 158, which in turn are welded or otherwise secured inside inner shell 142. The nozzle 154 and impingement surface 156 enable dual jet streams 104a and 104b to be directed at one another and interact in a shearing manner, rather than in a direct impingement manner. As discussed above, it is believed that shearing results in various forces that further break down the solid organic particles within the fluid suspension 104. The shearing forces also mix the sheared surfaces with surfactants provided in the suspension to coat and stabilize the newly formed particles. To that end, the elongated nature of the opposing fluid streams also provides a longer contact time for the mixing and coating to occur.

Nozzle 154 directs jet 104*a* inwardly toward the concave side of impingement surface 156. The concave nature of surface 156 tends to redirect stream 104*a* in the opposite direction. The convex side of surface 156 also directs stream 104*b* slightly outwardly so that streams 104*a* and 104*b* do not directly impinge one another. The nozzle 154 also aids in that endeavor. Nozzle 154 further aids in creating cavitation forces due to the acceleration of suspension fluid 104*a* entering and exiting the nozzle. Fluid streams 104*a* and 104*b* mix and combine to proceed along a path 160, which is opposite to the path of stream 104*a*.

Path 160 creates shear forces, impact forces and cavitation forces with the stream of suspension fluid 104*a* entering the system from nozzle 150. Apparatus 140 may increase the level of breakdown and mixing of the particles relative to that of FIGS. 18 and 19 because the velocity difference of the vectors of 104*a* and 160 is greater than that created by the high inner velocity stream and low outer velocity stream of FIGS. 18 and 19.

End cap 146 has a toroidal shape similar to the cross-section of a shell coating of a doughnut and is configured to redirect the inner annular stream 160 outward along an inner surface of inner shell 142, to form an outer annular stream 162. Outer annular stream 162 in turn shears against inner annular stream 160, creating further forces, further particle breakdown and mixing. Outer annular path 162 is forced eventually out of an exit orifice 164 defined by inner shell 142.

The space between inner and outer shells 142 and 144 creates an area where the cooling fluid 120 described above is injected via an inlet port 166 and mixed with the stabilized and comminuted particles. Cooling fluid 120 is any of the cooling fluids discussed above. The cooled and stabilized suspension then exits the outer shell 144 via port 168.

The apparatus 170 of FIG. 21 is similar to that of apparatus 140 of FIG. 20. Apparatus 170 includes inner and outer shells 172 and 174. Inner shell 172 is fitted with end caps 176 and 178. End cap 176 has the toroidal or doughnut shell cross-sectional shape described above in connection with end cap 146. Apparatus 170 further includes nozzles 180 and 182 welded respectively to end caps 176 and 178.

The primary difference between device 170 and device 140 is that device 170 does not provide an intermediate nozzle and impingement surface; rather, device 170 provides only an impingement surface 186 (which is larger than surface 156 of FIG. 20 in one embodiment). Impingement surface 186 is welded or otherwise attached to one or more thin (e.g., metal) plates 188, which is in turn welded to or otherwise attached to an inner surface of inner shell 172. Device 170 does not, therefore, have the flow-through nozzle characteristics of the nozzle 154 of device 140. The flow streams are precluded from impinging one another by the impingement surface 186.

Another difference is that the components of the suspension, rather than the pre-mixed suspension, are injected through nozzles 180 and 182. In the illustrated embodiment, the water and surfactant fluid stream 206 is injected through nozzle 180. The stream 206 impacts the concave side of surface 186. Surface 186 therefore tends to deflect flow of stream 206 in the opposite direction. The drug and solvent stream 204 is injected through nozzle 182 to create a jet stream that impinges the convex side of surface 186.

Jet stream 204 flows around surface 186 and mixes with the water and surfactant 206 to create an inner annular stream 190, which is at least partially mixed reacted at or near the impingement surface 186 to form the suspension of solid particles in water and surfactant. Stream 190 continues to mix with the water and surfactant stream 206 as the stream 190 continues towards end cap 176. The high shearing forces created by the oppositely vectored velocities of streams 206 and 190 further aid in precipitating, comminuting and stabilizing the components towards the formation of a suspension of stable particles.

End cap 176 diverts inner annular stream 190 outwardly to create outer annular stream 192. Outer annular stream 192 shears against inner annular stream 190 providing further desirable product size reduction, mixing and stabilization effects. The product warmed by the transfer of kinetic energy within the nozzles 180 and 182 and within shell 172, leaves shell 172 via exit orifice 194. Coolant 120 enters outer shell 174 through inlet port 196 and proceeds into a cavity created between inner and outer shells 172 and 174. Coolant 120 cools the suspension that leaves shell 172. The cooled, comminuted and stable suspension then exits the outer shell 172 via port 198.

It should be appreciated that apparatuses 140 and 170 make use of the substantial particle breakdown that occurs due to the nozzling effect of nozzles 150, 152, 180 and 182. Two nozzles are provided in the illustrated embodiment, however, any suitable number of nozzles is contemplated. In another embodiment, flow from a single nozzle can be teed into either end of the apparatuses 140 and 170 or divided via a manifold into multiple (i.e., more than two) inlet streams.

Referring now to FIGS. 22 and 23, a nozzle 200 of the present invention is illustrated. It should be appreciated from the foregoing discussion that the nozzling effect creates instant accelerations and increases forces due to cavitation. The cavitation occurs due to the difference in velocity between the velocity at the wall, which is relatively low and the velocity at the center of the nozzle, which is relatively high. Nozzle 200 includes a turbulating structure 210. Turbulating structure 210 is shown also in FIG. 23.

Turbulating structure 210 performs two functions. First, it creates turbulent flow, which increases mixing and the breaking down of the solid particles of the present invention. Further, it increases the surface area for creating shear forces between the zero velocity flow at the baffle surfaces and the high velocity flow between the surfaces.

Figure 23:
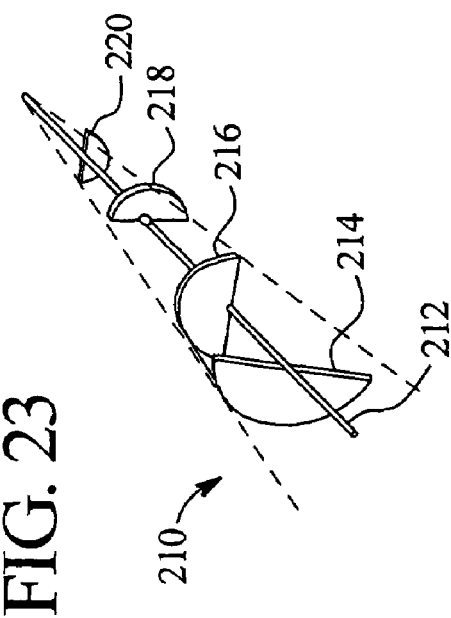
Figure 22:
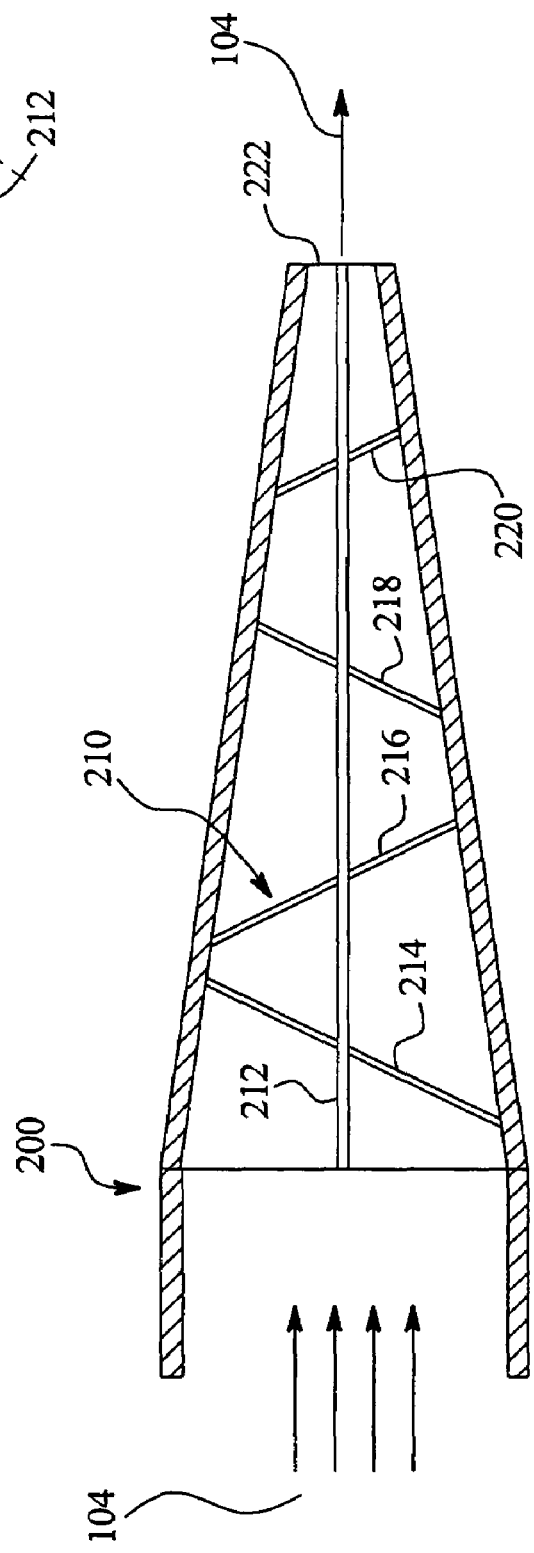
Figures 24, 25:
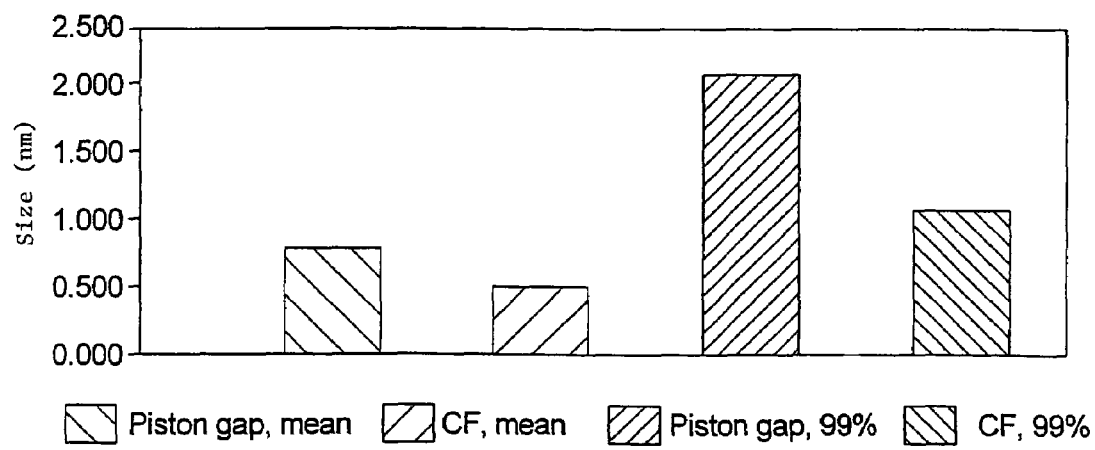

Turbulating structure 210 includes a centering rod 212 and baffles 214 to 220 connected, e.g., welded, thereto. As illustrated, the generally semicircle-shape of the baffles 214 to 220 decreases in radius so that the structure 210 fits within nozzle 200. Baffles 214 to 220 are welded or secured at an angle relative to 90° from the centering rod 212 in one embodiment. In alternative embodiments, the baffles are oriented at steeper or shallower angles than illustrated in FIG. 22 or are perpendicular relative to centering rod 212. FIG. 23 illustrates that the baffles 214 to 220 are also secured at different positions about the circumference of rod 212. In this manner, the baffles create a sequential, stepwise impingement to flow through nozzle 200.

It should be appreciated that for a given flowrate of suspension fluid 104 through nozzle 200, the open area of exit end 222 defines the exit velocity of the suspension fluid 104. That velocity is independent of whether or not nozzle 200 includes the turbulating structure 210. Device 210 therefore does not lessen the velocity of the exiting suspension fluid and, therefore, should not lessen the effect of the shearing forces described above due to oppositely oriented flowstreams located downstream from the nozzle. Turbulating structure 210 should however increase the amount of energy absorbed from intense pressures (e.g., 10,000 to 40,000 psig) from the pump driving the suspension or the components of the suspension.

Referring now to FIGS. 24 and 25, results from preparing one suspension fluid according to the apparatus and method of the present invention are illustrated. The results were obtained using an apparatus very similar to that illustrated in FIG. 18. FIG. 24 illustrates that the test suspension fluid contains Itraconazole, an antifungal, in an amount of 1%. The results of comminuting the suspension of FIG. 24 via the device of the present invention are compared in FIG. 25 with the results of comminuting the same suspension fluid via the piston-gap method discussed above.

FIG. 25 illustrates that the counterflow ("CF") system of the present invention yielded a smaller mean particle size than did the piston-gap method. Further, the counterflow system of the present invention produced a narrower particle distribution as shown by the smaller size of the upper 99% cumulative size distribution. The apparatuses and methods of the present invention, in combination with the particular particles and surfactants disclosed herein, therefore yield smaller and more consistently sized particles versus the piston-gap method.

Polymorph Control

The present invention further provides additional steps for controlling the crystal structure of an organic compound to ultimately produce a suspension of the compound in the desired size range and a desired crystal structure. What is meant by the term "crystal structure" is the arrangement of the atoms within the unit cell of the crystal. Compounds that can be crystallized into different crystal structures are said to be polymorphic. Identification of polymorphs is important step in drug formulation since different polymorphs of the same drug can show differences in solubility, therapeutic activity, bioavailability, and suspension stability. Accordingly, it is important to control the polymorphic form of the compound for ensuring product purity and batch-to-batch reproducibility.

The steps to control the polymorphic form of the compound includes seeding the first solution, the second solvent or the pre-suspension to ensure the formation of the desired polymorph. Seeding includes using a seed compound or adding energy. In a preferred form of the invention the seed compound is a pharmaceutically-active compound in the desired polymorphic form. Alternatively, the seed compound can also be an inert impurity, a compound unrelated in structure to the desired polymorph but with features that may lead to templating of a crystal nucleus, or an organic compound with a structure similar to that of the desired polymorph.

The seed compound can be precipitated from the first solution. This method includes the steps of adding the organic compound in sufficient quantity to exceed the solubility of the organic compound in the first solvent to create a supersaturated solution. The supersaturated solution is treated to precipitate the organic compound in the desired polymorphic form. Treating the supersaturated solution includes aging the solution for a time period until the formation of a crystal or crystals is observed to create a seeding mixture. It is also possible to add energy to the supersaturated solution to cause the organic compound to precipitate out of the solution in the desired polymorph. The energy can be added in a variety of ways including the energy addition steps described above. Further energy can be added by heating, or by exposing the pre-suspension to electromagnetic energy, particle beam or electron beam sources. The electromagnetic energy includes light energy (ultraviolet, visible, or infrared) or coherent radiation such as that provided by a laser, microwave energy such as that provided by a maser (microwave amplification by stimulated emission of radiation), dynamic electromagnetic energy, or other radiation sources. It is further contemplated utilizing ultrasound, a static electric field, or a static magnetic field, or combinations of these, as the energy-addition source.

In a preferred form of the invention, the method for producing seed crystals from an aged supersaturated solution includes the steps of: (i) adding a quantity of an organic compound to the first organic solvent to create a supersaturated solution, (ii) aging the supersaturated solution to form detectable crystals to create a seeding mixture; and (iii) mixing the seeding mixture with the second solvent to precipitate the organic compound to create a pre-suspension. The pre-suspension can then be further processed as described in detail above to provide an aqueous suspension of the organic compound in the desired polymorph and in the desired size range.

Seeding can also be accomplished by adding energy to the first solution, the second solvent or the pre-suspension provided that the exposed liquid or liquids contain the organic compound or a seed material. The energy can be added in the same fashion as described above for the supersaturated solution.

Accordingly, the present invention provides a composition of matter of an organic compound in a desired polymorphic form essentially free of the unspecified polymorph or polymorphs. In a preferred form of the present invention, the organic compound is a pharmaceutically active substance. One such example is set forth in example 16 below where seeding during microprecipitation provides a polymorph of itraconazole essentially free of the polymorph of the raw material. It is contemplated the methods of this invention can be used to selectively produce a desired polymorph for numerous pharmaceutically active compounds.

EXAMPLES

A. Examples of Process Category 1

Example 1

Preparation of Itraconazole Suspension by use of Process Category 1, Method A with Homogenization To a 3-L flask add 1680 mL of Water for Injection. Heat liquid to 60-65° C., and then slowly add 44 grams of Pluronic F-68 (poloxamer 188), and 12 grams of sodium deoxycholate, stirring after each addition to dissolve the solids. After addition of solids is complete, stir for another 15 minutes at 60-65° C. to ensure complete dissolution. Prepare a 50 mM tris (tromethamine) buffer by dissolving 6.06 grams of tris in 800 mL of Water for Injection. Titrate this solution to pH 8.0 with 0.1 M hydrochloric acid. Dilute the resulting solution to 1 liter with additional Water for Injection. Add 200 mL of the tris buffer to the poloxamer/deoxycholate solution. Stir thoroughly to mix solutions.

In a 150-mL beaker add 20 grams of itraconazole and 120 mL of N-methyl-2-pyrrolidinone. Heat mixture to 50-60° C., and stir to dissolve solids. After total dissolution is visually apparent, stir another 15 minutes to ensure complete dissolution. Cool itraconazole-NMP solution to room temperature.

Charge a syringe pump (two 60-mL glass syringes) with the 120-mL of itraconazole solution prepared previously. Meanwhile pour all of the surfactant solution into a homogenizer hopper that has been cooled to 0-5° C. (this may either by accomplished by use of a jacketed hopper through which refrigerant is circulated, or by surrounding the hopper with ice). Position a mechanical stirrer into the surfactant solution so that the blades are fully immersed. Using the syringe pump, slowly (1-3 mL/min) add all of the itraconazole solution to the stirred, cooled surfactant solution. A stirring rate of at least 700 rpm is recommended. An aliquot of the resulting suspension (Suspension A) is analyzed by light microscopy (Hoffman Modulation Contrast) and by laser diffraction (Horiba). Suspension A is observed by light microscopy to consist of roughly spherical amorphous particles (under 1 micron), either bound to each other in aggregates or freely moving by Brownian motion. See FIG. 3. Dynamic light scattering measurements typically afford a bimodal distribution pattern signifying the presence of aggregates (10-100 microns in size) and the presence of single amorphous particles ranging 200-700 nm in median particle diameter.

The suspension is immediately homogenized (at 10,000 to 30,000 psi) for 10-30 minutes. At the end of homogenization, the temperature of the suspension in the hopper does not exceed 75° C. The homogenized suspension is collected in 500-mL bottles, which are cooled immediately in the refrigerator (2-8° C.). This suspension (Suspension B) is analyzed by light microscopy and is found to consist of small elongated plates with a length of 0.5 to 2 microns and a width in the 0.2-1 micron range. See FIG. 4. Dynamic light scattering measurements typically indicate a median diameter of 200-700 nm.

Stability of Suspension A ("Pre-suspension") (Example 1)

During microscopic examination of the aliquot of Suspension A, crystallization of the amorphous solid was directly observed. Suspension A was stored at 2-8° C. for 12 hours and examined by light microscopy. Gross visual inspection of the sample revealed severe flocculation, with some of the contents settling to the bottom of the container. Microscopic examination indicated the presence of large, elongated, plate-like crystals over 10 microns in length.

Stability of Suspension B

As opposed to the instability of Suspension A, Suspension B was stable at 2-8° C. for the duration of the preliminary stability study (1 month). Microscopy on the aged sample clearly demonstrated that no significant change in the morphology or size of the particles had occurred. This was confirmed by light scattering measurement.

Example 2

Preparation of Itraconazole Suspension by use of Process Category 1, Method A with Ultrasonication To a 500-mL stainless steel vessel add 252 mL of Water for Injection. Heat liquid to 60-65° C., and then slowly add 6.6 grams of Pluronic F-68 (poloxamer 188), and 0.9 grams of sodium deoxycholate, stirring after each addition to dissolve the solids. After addition of solids is complete, stir for another 15 minutes at 60-65° C. to ensure complete dissolution. Prepare a 50 mM tris (tromethamine) buffer by dissolving 6.06 grams of tris in 800 mL of Water for Injection. Titrate this solution to pH 8.0 with 0.1 M hydrochloric acid. Dilute the resulting solution to 1 liter with additional Water for Injection. Add 30 mL of the tris buffer to the poloxamer/deoxycholate solution. Stir thoroughly to mix solutions.

In a 30-mL container add 3 grams of itraconazole and 18 mL of N-methyl-2-pyrrolidinone. Heat mixture to 50-60° C., and stir to dissolve solids. After total dissolution is visually apparent, stir another 15 minutes to ensure complete dissolution. Cool itraconazole-NMP solution to room temperature.

Charge a syringe pump with 18-mL of itraconazole solution prepared in a previous step. Position a mechanical stirrer into the surfactant solution so that the blades are fully immersed. Cool the container to 0-5° C. by immersion in an ice bath. Using the syringe pump, slowly (1-3 mL/min) add all of the itraconazole solution to the stirred, cooled surfactant solution. A stirring rate of at least 700 rpm is recommended. Immerse an ultrasonicator horn in the resulting suspension so that the probe is approximately 1 cm above the bottom of the stainless steel vessel. Sonicate (10,000 to 25,000 Hz, at least 400W) for 15 to 20 minute in 5-minute intervals. After the first 5-minute sonication, remove the ice bath and proceed with further sonication. At the end of ultrasonication, the temperature of the suspension in the vessel does not exceed 75° C.

The suspension is collected in a 500-mL Type I glass bottle, which is cooled immediately in the refrigerator (2-8° C.). Characteristics of particle morphology of the suspension before and after sonication were very similar to that seen in Method A before and after homogenization (see Example 1).

Example 3

Preparation of Itraconazole Suspension by use of Process Category 1, Method B with Homogenization.

Prepare a 50 mM tris (tromethamine) buffer by dissolving 6.06 grams of tris in 800 mL of Water for Injection. Titrate this solution to pH 8.0 with 0.1 M hydrochloric acid. Dilute the resulting solution to 1 liter with additional Water for Injection. To a 3-L flask add 1680 mL of Water for Injection. Add 200 mL of the tris buffer to the 1680 mL of water. Stir thoroughly to mix solutions.

In a 150-mL beaker add 44 grams of Pluronic F-68 (poloxamer 188) and 12 grams of sodium deoxycholate to 120 mL of N-methyl-2-pyrrolidinone. Heat the mixture to 50-60° C., and stir to dissolve solids. After total dissolution is visually apparent, stir another 15 minutes to ensure complete dissolution. To this solution, add 20 grams of itraconazole, and stir until totally dissolved. Cool the itraconazole-surfactant-NMP solution to room temperature.

Charge a syringe pump (two 60-mL glass syringes) with the 120-mL of the concentrated itraconazole solution prepared previously. Meanwhile pour the diluted tris buffer solution prepared above into a homogenizer hopper that has been cooled to 0-5° C. (this may either by accomplished by use of a jacketed hopper through which refrigerant is circulated, or by surrounding the hopper with ice). Position a mechanical stirrer into the buffer solution so that the blades are fully immersed. Using the syringe pump, slowly (1-3 mL/min) add all of the itraconazole-surfactant concentrate to the stirred, cooled buffer solution. A stirring rate of at least 700 rpm is recommended. The resulting cooled suspension is immediately homogenized (at 10,000 to 30,000 psi) for 10-30 minutes. At the end of homogenization, the temperature of the suspension in the hopper does not exceed 75° C.

The homogenized suspension is collected in 500-mL bottles, which are cooled immediately in the refrigerator (2-8° C.). Characteristics of particle morphology of the suspension before and after homogenization were very similar to that seen in Example 1, except that in process category 1 B, the pre-homogenized material tended to form fewer and smaller aggregates which resulted in a much smaller overall particle size as measured by laser diffraction. After homogenization, dynamic light scattering results were typically identical to those presented in Example 1.

Example 4

Preparation of Itraconazole Suspension by use of Process Category 1, Method B with Ultrasonication To a 500-mL flask add 252 mL of Water for Injection. Prepare a 50 mM tris (tromethamine) buffer by dissolving 6.06 grams of tris in 800 mL of Water for Injection. Titrate this solution to pH 8.0 with 0.1 M hydrochloric acid. Dilute the resulting solution to 1 liter with additional Water for Injection. Add 30 mL of the tris buffer to the water. Stir thoroughly to mix solutions.

In a 30-mL beaker add 6.6 grams of Pluronic F-68 (poloxamer 188) and 0.9 grams of sodium deoxycholate to 18 mL of N-methyl-2-pyrrolidinone. Heat the mixture to 50-60° C., and stir to dissolve solids. After total dissolution is visually apparent, stir another 15 minutes to ensure complete dissolution. To this solution, add 3.0 grams of itraconazole, and stir until totally dissolved. Cool the itraconazole-surfactant-NMP solution to room temperature.

Charge a syringe pump (one 30-mL glass syringe with the 18-mL of the concentrated itraconazole solution prepared previously. Position a mechanical stirrer into the buffer solution so that the blades are fully immersed. Cool the container to 0-5° C. by immersion in an ice bath. Using the syringe pump, slowly (1-3 mL/min) add all of the itraconazole-surfactant concentrate to the stirred, cooled buffer solution. A stirring rate of at least 700 rpm is recommended. The resulting cooled suspension is immediately sonicated (10,000 to 25,000 Hz, at least 400 W) for 15-20 minutes, in 5-minute intervals. After the first 5-minute sonication, remove the ice bath and proceed with further sonication. At the end of ultrasonication, the temperature of the suspension in the hopper does not exceed 75° C.

The resultant suspension is collected in a 500-mL bottle, which is cooled immediately in the refrigerator (2-8° C.). Characteristics of particle morphology of the suspension before and after sonication were very similar to that seen in Example 1, except that in Process Category 1, Method B, the pre-sonicated material tended to form fewer and smaller aggregates which resulted in a much smaller overall particle size as measured by laser diffraction. After ultrasonication, dynamic light scattering results were typically identical to those presented in Example 1

B. Examples of Process Category 2

Example 5

Preparation of Itraconazole Suspension (1%) with 0.75% Solutol® HR (PEG-660 12-Hydroxystearate) Process Category 2, Method B Solutol (2.25 g) and itraconazole (3.0 g) were weighed into a beaker and 36 mL of filtered N-methyl-2-pyrrolidinone (NMP) was added. This mixture was stirred under low heat (up to 40° C.) for approximately 15 minutes until the solution ingredients were dissolved. The solution was cooled to room temperature and was filtered through a 0.2-micron filter under vacuum. Two 60-mL syringes were filled with the filtered drug concentrate and were placed in a syringe pump. The pump was set to deliver approximately 1 mL/min of concentrate to a rapidly stirred (400 rpm) aqueous buffer solution. The buffer solution consisted of 22 g/L of glycerol in 5 mM tris buffer. Throughout concentrate addition, the buffer solution was kept in an ice bath at 2-3° C. At the end of the precipitation, after complete addition of concentrate to the buffer solution, about 100 mL of the suspension was centrifuged for 1 hour, the supernatant was discarded. The precipitate was resuspended in a 20% NMP solution in water, and again centrifuged for 1 hour. The material was dried overnight in a vacuum oven at 25° C. The dried material was transferred to a vial and analyzed by X-ray diffractometry using chromium radiation (see FIG. 5).

Another 100 mL-aliquot of the microprecipitated suspension was sonicated for 30 minutes at 20,000 Hz, 80% full amplitude (full amplitude =600 W). The sonicated sample was homogenized in 3 equal aliquots each for 45 minutes (Avestin C5, 2-5° C., 15,000-20,000 psi). The combined fractions were centrifuged for about 3 hours, the supernatant removed, and the precipitate resuspended in 20% NMP. The resuspended mixture was centrifuged again (15,000 rpm at 5° C.). The supernatant was decanted off and the precipitate was vacuum dried overnight at 25° C. The precipitate was submitted for analysis by X-ray diffractometry (see FIG. 5). As seen in FIG. 5, the X-ray diffraction patterns of processed samples, before and after homogenization, are essentially identical, yet show a significantly different pattern as compared with the starting raw material. The unhomogenized suspension is unstable and agglomerates upon storage at room temperature. The stabilization that occurs as a result of homogenization is believed to arise from rearrangement of surfactant on the surface of the particle. This rearrangement should result in a lower propensity for particle aggregation.

C. Examples of Process Category

Example 6

Preparation of Carbamazepine Suspension by use of Process Category 3, Method A with Homogenization 2.08 g of carbamazepine was dissolved into 10 mL of NMP. 1.0 mL of this concentrate was subsequently dripped at 0.1 mL/min into 20 mL of a stirred solution of 1.2% lecithin and 2.25% glycerin. The temperature of the lecithin system was held at 2-5° C. during the entire addition. The predispersion was next homogenized cold (5-15° C.) for 35 minutes at 15,000 psi. The pressure was increased to 23,000 psi and the homogenization was continued for another 20 minutes. The particles produced by the process had a mean diameter of 0.881 μm with 99% of the particles being less than 2.44 μm.

Example 7

Preparation of 1% Carbamazepine Suspension with 0.125% Solutolo® by use of Process Category 3, Method B with Homogenization A drug concentrate of 20% carbamazepine and 5% glycodeoxycholic acid (Sigma Chemical Co.) in N-methyl-2-pyrrolidinone was prepared. The microprecipitation step involved adding the drug concentrate to the receiving solution (distilled water) at a rate of 0.1 mL/min. The receiving solution was stirred and maintained at approximately 5° C. during precipitation. After precipitation, the final ingredient concentrations were 1% carbamazepine and 0.125% Solutolo®. The drug crystals were examined under a light microscope using positive phase contrast (400×). The precipitate consisted of fine needles approximately 2 microns in diameter and ranging from 50-150 microns in length.

Homogenization (Avestin C-50 piston-gap homogenizer) at approximately 20,000 psi for approximately 15 minutes results in small particles, less than 1 micron in size and largely unaggregated. Laser diffraction analysis (Horiba) of the homogenized material showed that the particles had a mean size of 0.4 micron with 99% of the particles less than 0.8 micron. Low energy sonication, suitable for breaking agglomerated particles, but not with sufficient energy to cause a comminution of individual particles, of the sample before Horiba analysis had no effect on the results (numbers were the same with and without sonication). This result was consistent with the absence of particle agglomeration.

Samples prepared by the above process were centrifuged and the supernatant solutions replaced with a replacement solution consisting of 0.125% Solutol®. After centrifugation and supernatant replacement, the suspension ingredient concentrations were 1% carbamazepine and 0.125% Solutol®. The samples were re-homogenized by piston-gap homogenizer and stored at 5° C. After 4 weeks storage, the suspension had a mean particle size of 0.751 with 99% less than 1.729. Numbers reported are from Horiba analysis on unsonicated samples.

Example 8

Preparation of 1% Carbamazepine Suspension with 0.06% Sodium Glycodeoxycholate and 0.06% Poloxamer 188 by use of Process Category 3 Method B with Homogenization A drug concentrate comprising 20% carbamazepine and 5% glycodeoxycholate in N-methyl-2-pyrrolidinone was prepared. The microprecipitation step involved adding the drug concentrate to the receiving solution (distilled water) at a rate of 0.1 mL/min. Thus the following examples demonstrate that adding a surfactant or other excipient to the aqueous precipitating solution in Methods A and B above is optional. The receiving solution was stirred and maintained at approximately 5° C. during precipitation. After precipitation, the final ingredient concentrations were 1% carbamazepine and 0.125% Solutol®. The drug crystals were examined under a light microscope using positive phase contrast (400×). The precipitate consisted of fine needles approximately 2 microns in diameter and ranging from 50-150 microns in length. Comparison of the precipitate with the raw material before precipitation reveals that the precipitation step in the presence of surface modifier (glycodeoxycholic acid) results in very slender crystals that are much thinner than the starting raw material (see FIG. 6).

Homogenization (Avestin C-50 piston-gap homogenizer) at approximately 20,000 psi for approximately 15 minutes results in small particles, less than 1 micron in size and largely unaggregated. See FIG. 7. Laser diffraction analysis (Horiba) of the homogenized material showed that the particles had a mean size of 0.4 micron with 99% of the particles less than 0.8 micron. Sonication of the sample before Horiba analysis had no effect on the results (numbers were the same with and without sonication). This result was consistent with the absence of particle agglomeration.

Samples prepared by the above process were centrifuged and the supernatant solutions replaced with a replacement solution consisting of 0.06% glycodeoxycholic acid (Sigma Chemical Co.) and 0.06% Poloxamer 188. The samples were re-homogenized by piston-gap homogenizer and stored at 5° C. After 2 weeks storage, the suspension had a mean particle size of 0.531 micron with 99% less than 1.14 micron. Numbers reported are from Horiba analysis on unsonicated samples.

Mathematical Analysis (Example 8) of force required to break precipitated particles as compared to force required to break particles of the starting raw material (carbamazepine):

The width of the largest crystals seen in the carbamazepine raw material (FIG. 6, picture on left) are roughly 10-fold greater than the width of crystals in the microprecipitated material (FIG. 6, picture on right). On the assumption that the ratio of crystal thickness (1:10) is proportional to the ratio of crystal width (1:10), then the moment of force required to cleave the larger crystal in the raw material should be approximately 1,000-times greater than the force needed to break the microprecipitated material, since:

$$e_L = 6PL/(Ewx^2) \qquad \text{Eq. 1}$$

where, $e_L$=longitudinal strain required to break the crystal ("yield value")

P=load on beam

L=distance from load to fulcrum

E=elasticity modulus w=width of crystal x=thickness of crystal

Let us assume that L and E are the same for the raw material and the precipitated material. Additionally, let us assume that $w/w_0 = x/x_0 = 10$. Then, $(e_L)_0 = 6P_0L/(Ew_0x_0^2)$, where the '0' subscripts refer to raw material $e_L = 6PL/(Ewx^2)$, for the microprecipitate Equating $(e_L)_0$ and $e_L$, $$6PL/(Ewx^2)=6P_0L/(Ew_0x_0^2)$$

After simplification, $$P=P_0(w/w_0)(x/x_0)^2=P_0(0.1)(0.1)^2=0.001P_0$$

Thus, the yield force, P, required to break the microprecipitated solid is one-thousandth the required force necessary to break the starting crystalline solid. If, because of rapid precipitation, lattice defects or amorphous properties are introduced, then the modulus (E) should decrease, making the microprecipitate even easier to cleave.

Example 9

Preparation of 1.6% (w/v) Prednisolone Suspension with 0.05% Sodium Deoxycholate and 3% N-methyl-2-pyrrolidinone Process Category 3, Method B A schematic of the overall manufacturing process is presented in FIG. 8. A concentrated solution of prednisolone and sodium deoxycholate was prepared. Prednisolone (32g) and sodium deoxycholate (1g) were added to a sufficient volume of 1-methyl 2-pyrrolidinone (NMP) to produce a final volume of 60 mL. The resulting prednisolone concentration was approximately 533.3 mg/mL and the sodium deoxycholate concentration was approximately 16.67 mg/mL. 60 mL of NMP concentrate was added to 2 L of water cooled to 5° C. at an addition rate of 2.5 mL/min while stirring at approximately 400 rpm. The resulting suspension contained slender needle-shaped crystals less than 2 μm in width (FIG. 9). The concentration contained in the precipitated suspension was 1.6% (w/v) prednisolone, 0.05% sodium deoxycholate, and 3% NMP.

The precipitated suspension was pH adjusted to 7.5-8.5 using sodium hydroxide and hydrochloric acid then homogenized (Avestin C-50 piston-gap homogenizer) for 10 passes at 10,000 psi. The NMP was removed by performing 2 successive centrifugation steps replacing the supernatant each time with a fresh surfactant solution, which contained the desired concentrations of surfactants needed to stabilize the suspension (see Table 2). The suspension was homogenized for another 10 passes at 10,000 psi. The final suspension contained particles with a mean particle size of less than 1 μm, and 99% of particles less than 2 μm. FIG. 10 is a photomicrograph of the final prednisolone suspension after homogenization.

A variety of different surfactants at varying concentrations were used in the centrifugation/surfactant replacement step (see Table 2). Table 2 lists combinations of surfactants that were stable with respect to particle size (mean <1 μm, 99% <2 μm), pH (6-8), drug concentration (less than 2% loss) and re-suspendability (resuspended in 60 seconds or less).

Notably this process allows for adding the active compound to an aqueous diluent without the presence of a surfactant or other additive. This is a modification of process Method B in FIG. 2.

TABLE 2

List of stable prednisolone suspensions prepared by microprecipitation process of FIG. 8 (Example 9)

|  | Initial | | 2 Weeks | | 2 Months | | | | | | |
|---|---|---|---|---|---|---|---|---|---|---|---|
|  |  |  | 40° C. | | 5° C. | | 25° C. | | 40° C. | | |
| Formulation | Mean | >99% | Mean | >99% | Mean | >99% | Mean | >99% | Mean | >99% | % Loss* |
| 1.6% prednisolone, 0.6% phospholipids, 0.5% sodium deoxycholate, 5 mM TRIS, 2.2% glycerol** | 0.79 | 1.65 | 0.84 | 1.79 | 0.83 | 1.86 | 0.82 | 1.78 | 0.82 | 1.93 | <2% |
| 1.6% prednisolone, 0.6% Solutol ®, 0.5% sodium deoxycholate, 2.2% glycerol | 0.77 | 1.52 | 0.79 | 1.67 | 0.805 | 1.763 | 0.796 | 1.693 | 0.81 | 1.633 | <2% |
| 1.6% prednisolone, 0.1% poloxamer 188, 0.5% sodium deoxycholate, 2.2% glycerol | 0.64 | 1.16 | 0.82 | 1.78 | 0.696 | 1.385 | 0.758 | 1.698 | 0.719 | 1.473 | <2% |
| 1.6% prednisolone, 5% phospholipids, 5 mM TRIS, 2.2% glycerol | 0.824 | 1.77 | 0.87 | 1.93 | 0.88 | 1.95 | 0.869 | 1.778 | 0.909 | 1.993 | <2% |

*Difference in itraconazole concentration between samples stored for 2 months at 5 and 25° C.
**Stable through at least 6 months.

Particle sizes (by laser light scattering), in microns:
5° C.: 0.80 (mean), 1.7 (99%)
25° C.: 0.90 (mean); 2.51 (99%)
40° C.: 0.99 (mean); 2.03 (99%)

Difference in itraconazole concentration between samples stored at 5 and 25° C.: <2%

Example 10

Preparation of Prednisolone Suspension by use of Process Category 3, Method A with Homogenization 32 g of prednisolone was dissolved into 40 mL of NMP. Gentle heating at 40-50° C. was required to effect dissolution. The drug NMP concentrate was subsequently dripped at 2.5 mL/min into 2 liters of a stirred solution that consisted of 0.1.2% lecithin and 2.2% glycerin. No other surface modifiers were added. The surfactant system was buffered at pH=8.0 with 5 mM tris buffer and the temperature was held at 0° to 5° C. during the entire precipitation process. The post-precipitated dispersion was next homogenized cold (5-15 °C.) for 20 passes at 10,000 psi. Following homogenization, the NMP was removed by centrifuging the suspension, removing the supernatant, and replacing the supernatant with fresh surfactant solution. This post-centrifuged suspension was then rehomogenized cold (5-15 ° C.) for another 20 passes at 10,000 psi. The particles produced by this process had a mean diameter of 0.927 μm with 99% of the particles being less than 2.36 μm.

Example 11

Preparation of Nabumetone Suspension by use of Process Category 3, Method B with Homogenization Surfactant (2.2 g of poloxamer 188) was dissolved in 6 mL of N-methyl-2-pyrrolidinone. This solution was stirred at 45° C. for 15 minutes, after which 1.0 g of nabumetone was added. The drug dissolved rapidly. Diluent was prepared which consisted of 5 mM tris buffer with 2.2% glycerol, and adjusted to pH 8. A 100-mL portion of diluent was cooled in an ice bath. The drug concentrate was slowly added (approximately 0.8 mL/min) to the diluent with vigorous stirring. This crude suspension was homogenized at 15,000 psi for 30 minutes and then at 20,000 psi for 30 minutes (temperature=5° C.). The final nanosuspension was found to be 930 nm in effective mean diameter (analyzed by laser diffraction). 99% of the particles were less than approximately 2.6 microns.

Example 12

Preparation of Nabumetone Suspension by use of Process Category 3, Method B with Homogenization and the use of Solutol® HS 15 as the Surfactant.

Replacement of Supernatant Liquid with a Phospholipid Medium.

Nabumetone (0.987 grams) was dissolved in 8 mL of N-methyl-2-pyrrolidinone. To this solution was added 2.2 grams of Solutol® HS 15. This mixture was stirred until complete dissolution of the surfactant in the drug concentrate. Diluent was prepared, which consisted of 5 mM tris buffer with 2.2% glycerol, and which was adjusted to pH 8. The diluent was cooled in an ice bath, and the drug concentrate was slowly added (approximately 0.5 mL/min) to the diluent with vigorous stirring. This crude suspension was homogenized for 20 minutes at 15,000 psi, and for 30 minutes at 20,000 psi.

The suspension was centrifuged at 15,000 rpm for 15 minutes and the supernatant was removed and discarded. The remaining solid pellet was resuspended in a diluent consisting of 1.2% phospholipids. This medium was equal in volume to the amount of supernatant removed in the previous step. The resulting suspension was then homogenized at approximately 21,000 psi for 30 minutes. The final suspension was analyzed by laser diffraction and was found to contain particles with a mean diameter of 542 nm, and a 99% cumulative particle distribution sized less than 1 micron.

Example 13

Preparation of 1% Itraconazole Suspension with Poloxamer with Particles of a Mean Diameter of Approximately 220 nm Itraconazole concentrate was prepared by dissolving 10.02 grams of itraconazole in 60 mL of N-methyl-2-pyrrolidinone. Heating to 70° C. was required to dissolve the drug. The solution was then cooled to room temperature. A portion of 50 mM tris(hydroxymethyl)aminomethane buffer (tris buffer) was prepared and was pH adjusted to 8.0 with SM hydrochloric acid. An aqueous surfactant solution was prepared by combining 22 g/L poloxamer 407, 3.0 g/L egg phosphatides, 22g/L glycerol, and 3.0 g/L sodium cholate dihydrate. 900 mL of the surfactant solution was mixed with 100 mL of the tris buffer to provide 1000 mL of aqueous diluent.

The aqueous diluent was added to the hopper of the homogenizer (APV Gaulin Model 15MR-8TA), which was cooled by using an ice jacket. The solution was rapidly stirred (4700 rpm) and the temperature was monitored. The itraconazole concentrate was slowly added, by use of a syringe pump, at a rate of approximately 2 mL/min. Addition was complete after approximately 30 minute. The resulting suspension was stirred for another 30 minutes while the hopper was still being cooled in an ice jacket, and an aliquot was removed for analysis by light microscopy any dynamic light scatting. The remaining suspension was subsequently homogenized for 15 minutes at 10,000 psi. By the end of the homogenization the temperature had risen to 74° C. The homogenized suspension was collected in a 1-L Type I glass bottle and sealed with a rubber closure. The bottle containing suspension was stored in a refrigerator at 5° C.

A sample of the suspension before homogenization showed the sample to consist of both free particles, clumps of particles, and multilamellar lipid bodies. The free particles could not be clearly visualized due to Brownian motion; however, many of the aggregates appeared to consist of amorphous, non-crystalline material.

The homogenized sample contained free submicron particles having excellent size homogeneity without visible lipid vesicles. Dynamic light scattering showed a monodisperse logarithmic size distribution with a median diameter of approximately 220 nm. The upper 99% cumulative size cutoff was approximately 500 nm. FIG. 11 shows a comparison of the size distribution of the prepared nanosuspension with that of a typical parenteral fat emulsion product (10% Intralipid®, Pharmacia).

Example 14

Preparation of 1% Itraconazole Nanosuspension with Hydroxyethylstarch

Preparation of Solution A: Hydroxyethylstarch (1 g, Ajinomoto) was dissolved in 3 mL of N-methyl-2-pyrrolidinone (NMP). This solution was heated in a water bath to 70-80° C. for 1 hour. In another container was added 1 g of itraconazole (Wyckoff). Three mL of NMP were added and the mixture heated to 70-80° C. to effect dissolution (approximately 30 minutes). Phospholipid (Lipoid S-100) was added to this hot solution. Heating was continued at 70-90° C. for 30 minutes until all of the phospholipid was dissolved. The hydroxyethylstarch solution was combined with the itraconazole/ phospholipid solution. This mixture was heated for another 30 minutes at 80-95° C. to dissolve the mixture.

Addition of Solution A to Tris Buffer: Ninety-four (94) mL of 50 mM tris(hydroxymethyl)aminomethane buffer was cooled in an ice bath. As the tris solution was being rapidly stirred, the hot Solution A (see above) was slowly added dropwise (less than 2 cc/minute).

After complete addition, the resulting suspension was sonicated (Cole-Parmer Ultrasonic Processor—20,000 Hz, 80% amplitude setting) while still being cooled in the ice bath. A one-inch solid probe was utilized. Sonication was continued for 5 minutes. The ice bath was removed, the probe was removed and retuned, and the probe was again immersed in the suspension. The suspension was sonicated again for another 5 minutes without the ice bath. The sonicator probe was once again removed and retuned, and after immersion of the probe the sample was sonicated for another 5 minutes. At this point, the temperature of the suspension had risen to 82° C. The suspension was quickly cooled again in an ice bath and when it was found to be below room temperature it was poured into a Type I glass bottle and sealed. Microscopic visualization of the particles indicated individual particle sizes on the order of one micron or less.

After one year of storage at room temperature, the suspension was reevaluated for particle size and found to have a mean diameter of approximately 300 nm.

Example 15

Prophetic Example of Method A Using HES

The present invention contemplates preparing a 1% itraconazole nanosuspension with hydroxyethylstarch utilizing Method A by following the steps of Example 14 with the exception the HES would be added to the tris buffer solution instead of to the NMP solution. The aqueous solution may have to be heated to dissolve the HES.

Example 16

Seeding During Homogenization to Convert a Mixture of Polymorphs to the More Stable Polymorph Sample preparation. An itraconazole nanosuspension was prepared by a microprecipitation-homogenization method as follows. Itraconazole (3 g) and Solutol HR (2.25 g) were dissolved in 36mL of N-methyl-2-pyrrolidinone (NMP) with low heat and stirring to form a drug concentrate solution. The solution was cooled to room temperature and filtered through a 0.2 μm nylon filter under vacuum to remove undissolved drug or particulate matter. The solution was viewed under polarized light to ensure that no crystalline material was present after filtering. The drug concentrate solution was then added at 1.0 mL/minute to approximately 264 mL of an aqueous buffer solution (22 g/L glycerol in 5 mM tris buffer). The aqueous solution was kept at 2-3° C. and was continuously stirred at approximately 400 rpm during the drug concentrate addition. Approximately 100 mL of the resulting suspension was centrifuged and the solids resuspended in a pre-filtered solution of 20% NMP in water. This suspension was re-centrifuged and the solids were transferred to a vacuum oven for overnight drying at 25° C. The resulting solid sample was labeled SMP 2 PRE.

Sample characterization. The sample SMP 2 PRE and a sample of the raw material itraconazole were analyzed using powder x-ray diffractometry. The measurements were performed using a Rigaku MiniFlex+ instrument with copper radiation, a step size of 0.02° 2θ and scan speed of 0.25° 2θ/minute. The resulting powder diffraction patterns are shown in FIG. 12. The patterns show that SMP-2-PRE is significantly different from the raw material, suggesting the presence of a different polymorph or a pseudopolymorph.

Differential scanning calorimetry (DSC) traces for the samples are shown in FIGS. 13a and b. Both samples were heated at 2°/min to 180° C. in hermetically sealed aluminum pans.

The trace for the raw material itraconazole (FIG. 13a) shows a sharp endotherm at approximately 165° C.

The trace for SMP 2 PRE (FIG. 13b) exhibits two endotherms at approximately 159° C. and 153° C. This result, in combination with the powder x-ray diffraction patterns, suggests that SMP 2 PRE consists of a mixture of polymorphs, and that the predominant form is a polymorph that is less stable than polymorph present in the raw material.

Further evidence for this conclusion is provided by the DSC trace in FIG. 14, which shows that upon heating SMP 2 PRE through the first transition, then cooling and reheating, the less stable polymorph melts and recrystallizes to form the more stable polymorph.

Seeding. A suspension was prepared by combining 0.2 g of the solid SMP 2 PRE and 0.2 g of raw material itraconazole with distilled water to a final volume of 20 mL (seeded sample). The suspension was stirred until all the solids were wetted. A second suspension was prepared in the same manner but without adding the raw material itraconazole (unseeded sample). Both suspensions were homogenized at approximately 18,000 psi for 30 minutes. Final temperature of the suspensions after homogenization was approximately 30° C. The suspensions were then centrifuged and the solids dried for approximately 16 hours at 30° C.

FIG. 15 shows the DSC traces of the seeded and unseeded samples. The heating rate for both samples was 2°/min to 180° C. in hermetically sealed aluminum pans. The trace for the unseeded sample shows two endotherms, indicating that a mixture of polymorphs is still present after homogenization. The trace for the seeded sample shows that seeding and homogenization causes the conversion of the solids to the stable polymorph. Therefore, seeding appears to influence the kinetics of the transition from the less stable to the more stable polymorphic form.

Example 17

Seeding During Precipitation to Preferentially Form a Stable Polymorph

Sample preparation. An itraconazole-NMP drug concentrate was prepared by dissolving 1.67 g of itraconazole in 10 mL of NMP with stirring and gentle heating. The solution was filtered twice using 0.2 μm syringe filters. Itraconazole nanosuspensions were then prepared by adding 1.2 mL of the drug concentrate to 20 mL of an aqueous receiving solution at approx. 3° C. and stirring at approx. 500 rpm. A seeded nanosuspension was prepared by using a mixture of approx. 0.02 g of raw material itraconazole in distilled water as the receiving solution. An unseeded nanosuspension was prepared by using distilled water only as the receiving solution. Both suspensions were centrifuged, the supernatants decanted, and the solids dried in a vacuum oven at 30° C. for approximately 16 hours.

Sample characterization. FIG. 16 shows a comparison of the DSC traces for the solids from the seeded and unseeded suspensions. The samples were heated at 2°/min to 180° C. in hermetically sealed aluminum pans. The dashed line represents the unseeded sample, which shows two endotherms, indicating the presence of a polymorphic mixture.

The solid line represents the seeded sample, which shows only one endotherm near the expected melting temperature of the raw material, indicating that the seed material induced the exclusive formation of the more stable polymorph.

Example 18

Polymorph Control by Seeding the Drug Concentrate

Sample preparation. The solubility of itraconazole in NMP at room temperature (approximately 22° C.) was experimentally determined to be 0.16 g/mL. A 0.20 g/mL drug concentrate solution was prepared by dissolving 2.0 g of itraconazole and 0.2 g Poloxamer 188 in 10 mL NMP with heat and stirring. This solution was then allowed to cool to room temperature to yield a supersaturated solution. A microprecipitation experiment was immediately performed in which 1.5 mL of the drug concentrate was added to 30 mL of an aqueous solution containing 0.1% deoxycholate, 2.2% glycerol. The aqueous solution was maintained at ~2° C. and a stir rate of 350 rpm during the addition step. The resulting presuspension was homogenized at ~13,000 psi for approx. 10 minutes at 50° C. The suspension was then centrifuged, the supernatant decanted, and the solid crystals dried in a vacuum oven at 30° C. for 135 hours.

The supersaturated drug concentrate was subsequently aged by storing at room temperature in order to induce crystallization. After 12 days, the drug concentrate was hazy, indicating that crystal formation had occurred. An itraconazole suspension was prepared from the drug concentrate, in the same manner as in the first experiment, by adding 1.5 mL to 30 mL of an aqueous solution containing 0.1% deoxycholate, 2.2% glycerol. The aqueous solution was maintained at ~5° C. and a stir rate of 350 rpm during the addition step. The resulting presuspension was homogenized at ~13,000 psi for approx. 10 minutes at 50° C. The suspension was then centrifuged, the supernatant decanted, and the solid crystals dried in a vacuum oven at 30° C. for 135 hours.

Sample characterization. X-ray powder diffraction analysis was used to determine the morphology of the dried crystals. The resulting patterns are shown in FIG. 17. The crystals from the first experiment (using fresh drug concentrate) were determined to consist of the more stable polymorph. In contrast, the crystals from the second experiment (aged drug concentrate) were predominantly composed of the less stable polymorph, with a small amount of the more stable polymorph also present. Therefore, it is believed that aging induced the formation of crystals of the less stable polymorph in the drug concentrate, which then acted as seed material during the microprecipitation and homogenization steps such that the less stable polymorph was preferentially formed.

While specific embodiments have been illustrated and described, numerous modifications come to mind without departing from the spirit of the invention and the scope of protection is only limited by the scope of the accompanying claims.

What is claimed is:

1. A method for preparing a nanoparticle suspension comprising the steps of:
   providing a comminuting apparatus with a chamber;
   dissolving an organic compound in a water miscible first solvent to create a first solution;
   mixing said first solution with a second solvent to precipitate the organic compound to create a suspension of particles outside of said chamber of said comminuting apparatus;
   introducing said suspension into said chamber of said comminuting apparatus;
   moving said suspension through said chamber in a first fluid stream and in a first direction;
   contacting said first fluid stream with an impacting surface; and
   redirecting the first fluid stream to flow in a second fluid stream in a second direction that is substantially opposite to said first direction, to cause shearing between the streams and mixing of at least some of the particles from the first and second streams.

2. The method of claim 1 further comprising cooling said second stream.

3. The method of claim 2 comprising cooling said second stream by adding water to said second stream.

4. The method of claim 3 comprising cooling said second stream when said second stream is no longer in contact with said first stream.

5. The method of claim 2 comprising cooling said second stream by mixing said second stream with a liquid.

6. The method of claim 1 comprising contacting said first fluid stream with a semi-spherical impacting surface.

7. The method of claim 1 comprising contacting said first fluid stream with a substantially flat surface.

8. A method for modifying a particle suspension comprising the steps of:
   moving a suspension of solid particles from a first entrance point in a first fluid stream;
   moving fluid from a second entrance point in a second fluid stream, said second entrance point being substantially oppositely disposed relative to said first entrance point; and
   contacting at least one of said first and second streams with an obstruction disposed between said first and second entrance points to redirect at least one of said first and second streams such that said second fluid stream is oriented to cause shearing between the streams and mixing of at least some of the particles the first and second streams.

9. The method of claim 8 further comprising contacting at least one of said first and second streams with an obstruction having a first contacting surface and a second contacting surface.

10. The method of claim 9 further comprising contacting said first stream with said first contacting surface and contacting said second stream with said second contacting surface.

11. The method of claim 10 comprising contacting said second stream with said second contacting surface to redirect said second stream and avoid direct impingement of said first and second streams.

12. The method of claim 10 further comprising passing said first stream through a nozzle disposed between said first entrance point and said obstruction.

13. The method of claim 8 comprising contacting said first and second streams with a first impacting surface.

14. The method of claim 13 further comprising contacting at least one of said first and second streams with a second impacting surface to redirect at least one of said first and second streams.

* * * * *